US009426996B2

(12) United States Patent
Maclean et al.

(10) Patent No.: US 9,426,996 B2
(45) Date of Patent: Aug. 30, 2016

(54) USE OF BENZOXABOROLES AS VOLATILE ANTIMICROBIAL AGENTS ON MEATS, PLANTS, OR PLANT PARTS

(71) Applicant: AgroFresh Inc., Collegeville, PA (US)

(72) Inventors: Daniel Maclean, Woodland, CA (US); David H. Young, Carmel, IN (US); Richard M. Jacobson, Chalfont, PA (US); Maurice C. Yap, Zionsville, IN (US); Rodrigo A. Cifuentes, Santiago (CL); Donald H. DeVries, Fishers, IN (US); Joseph D. Eckelbarger, Carmel, IN (US)

(73) Assignee: AgroFresh Inc., Collegeville, PA (US)

( * ) Notice: Subject to any disclaimer, the term of this patent is extended or adjusted under 35 U.S.C. 154(b) by 0 days.

(21) Appl. No.: 14/294,057

(22) Filed: Jun. 2, 2014

(65) Prior Publication Data
US 2014/0349853 A1 Nov. 27, 2014

Related U.S. Application Data

(63) Continuation of application No. 14/167,093, filed on Jan. 29, 2014, now Pat. No. 9,138,001.

(60) Provisional application No. 61/758,313, filed on Jan. 30, 2013.

(51) Int. Cl.
*A01N 55/08* (2006.01)
*A01N 3/02* (2006.01)
*A23B 4/20* (2006.01)
*A23B 7/154* (2006.01)
*A01N 27/00* (2006.01)
*A23B 4/16* (2006.01)
*A23B 7/152* (2006.01)

(52) U.S. Cl.
CPC .............. *A01N 55/08* (2013.01); *A01N 3/02* (2013.01); *A01N 27/00* (2013.01); *A23B 4/16* (2013.01); *A23B 4/20* (2013.01); *A23B 7/152* (2013.01); *A23B 7/154* (2013.01)

(58) Field of Classification Search
CPC .................................................... A01N 55/08
USPC ......................................................... 549/213
See application file for complete search history.

(56) References Cited

U.S. PATENT DOCUMENTS

| 3,686,398 | A | 8/1972 | Kohn et al. |
|---|---|---|---|
| 3,873,279 | A | 3/1975 | Singer |
| 5,880,188 | A | 3/1999 | Austin et al. |
| 7,390,806 | B2 | 6/2008 | Lee et al. |
| 7,393,856 | B2 | 7/2008 | Bellinger-Kawahara et al. |
| 7,465,836 | B2 | 12/2008 | Lee et al. |
| 7,582,621 | B2 | 9/2009 | Baker et al. |
| 7,652,000 | B2 | 1/2010 | Perry et al. |
| 7,767,657 | B2 | 8/2010 | Baker et al. |
| 7,816,344 | B2 | 10/2010 | Baker et al. |
| 7,888,356 | B2 | 2/2011 | Lee et al. |
| 7,968,752 | B2 | 6/2011 | Lee et al. |
| 8,039,450 | B2 | 10/2011 | Akama et al. |
| 8,039,451 | B2 | 10/2011 | Baker et al. |
| 8,106,031 | B2 | 1/2012 | Lee et al. |
| 8,115,026 | B2 | 2/2012 | Baker et al. |
| 8,168,614 | B2 | 5/2012 | Baker et al. |
| 8,343,944 | B2 | 1/2013 | Xia et al. |
| 8,440,642 | B2 | 5/2013 | Baker et al. |
| 8,461,134 | B2 | 6/2013 | Hernandez et al. |
| 8,461,135 | B2 | 6/2013 | Akama et al. |
| 8,461,336 | B2 | 6/2013 | Zhou et al. |
| 8,461,364 | B2 | 6/2013 | Wheeler et al. |
| 8,470,803 | B2 | 6/2013 | Akama et al. |
| 8,501,712 | B2 | 8/2013 | Baker et al. |
| 8,546,357 | B2 | 10/2013 | Akama et al. |
| 8,669,207 | B1 | 3/2014 | Jacobson et al. |
| 2004/0259842 | A1 | 12/2004 | Mikoshiba et al. |
| 2007/0155699 | A1* | 7/2007 | Baker et al. ............. 514/64 |
| 2007/0286822 | A1* | 12/2007 | Sanders et al. ............. 424/49 |
| 2007/0293457 | A1 | 12/2007 | Baker et al. |
| 2008/0153992 | A1 | 6/2008 | Knott et al. |
| 2008/0293675 | A1 | 11/2008 | Lee et al. |
| 2008/0317737 | A1 | 12/2008 | Patel et al. |
| 2009/0227541 | A1 | 9/2009 | Baker et al. |
| 2009/0239824 | A1 | 9/2009 | Lee et al. |
| 2009/0291917 | A1 | 11/2009 | Akama et al. |
| 2010/0158992 | A1 | 6/2010 | Black et al. |

(Continued)

FOREIGN PATENT DOCUMENTS

| AU | 2010203096 B2 | 2/2010 |
|---|---|---|
| AU | 2012327171 A1 | 6/2013 |

(Continued)

OTHER PUBLICATIONS

J. Med. Chem. (2011), vol. 54(5), pp. 1276-1287.*
Submitted to applicant in the parent U.S. Appl. No. 14/167,093.*
Shen et al., Zhongguo Nongye Daxue Xuebao (2004) vol. 9(2), pp. 36-39.*
Guillen et al., Postharvest Biology and Technol. (2006) vol. 42(3), pp. 235-242.*
Garillo et al., LWT-Food Sci. and Tech. (2011) vol. 44, pp. 250-255.*
Brown et al., Proc. for Prepn. Alkyl Borate Esters, (1956), pp. 3613-3614.*

(Continued)

*Primary Examiner* — Taofiq A Solola
(74) *Attorney, Agent, or Firm* — Taft Stettinius & Hollister LLP; Gregory B. Coy

(57) ABSTRACT

This invention is related to use of a volatile antimicrobial compound against pathogens affecting meats, plants, or plant parts. The volatile antimicrobial compounds provided include certain oxaborole compounds, for example benzoxaboroles. Delivery systems are provided to take advantage of the volatile nature of these antimicrobial compounds. Also combinations with a volatile plant growth regulator, for example 1-methylcyclopropene, are disclosed.

18 Claims, 4 Drawing Sheets

(56) References Cited

U.S. PATENT DOCUMENTS

| | | |
|---|---|---|
| 2010/0190748 A1 | 7/2010 | Baker et al. |
| 2010/0256092 A1 | 10/2010 | Xia et al. |
| 2010/0267981 A1 | 10/2010 | Baker et al. |
| 2010/0292504 A1 | 11/2010 | Baker et al. |
| 2011/0059985 A1 | 3/2011 | Schmidts et al. |
| 2011/0076261 A1 | 3/2011 | Patel et al. |
| 2011/0082118 A1 | 4/2011 | Patel et al. |
| 2011/0123624 A1* | 5/2011 | Zasloff .......................... 424/489 |
| 2011/0124597 A1 | 5/2011 | Hernandez et al. |
| 2011/0136763 A1 | 6/2011 | Xia et al. |
| 2011/0152217 A1 | 6/2011 | Wheeler et al. |
| 2011/0166103 A1 | 7/2011 | Akama et al. |
| 2011/0166104 A1 | 7/2011 | Zhou et al. |
| 2011/0172187 A1 | 7/2011 | Hernandez et al. |
| 2011/0190235 A1 | 8/2011 | Chen et al. |
| 2011/0207701 A1 | 8/2011 | Zhou et al. |
| 2011/0207702 A1 | 8/2011 | Jacobs et al. |
| 2011/0212918 A1 | 9/2011 | Hernandez et al. |
| 2011/0319361 A1 | 12/2011 | Baker et al. |
| 2012/0035132 A1 | 2/2012 | Jarnagin et al. |
| 2012/0115813 A1 | 5/2012 | Hernandez et al. |
| 2012/0214765 A1 | 8/2012 | Akama et al. |
| 2012/0264714 A1 | 10/2012 | Baker et al. |
| 2012/0289686 A1 | 11/2012 | Baker et al. |
| 2012/0295875 A1 | 11/2012 | Zhou et al. |
| 2013/0059802 A1 | 3/2013 | Baker et al. |
| 2013/0059803 A1 | 3/2013 | Baker et al. |
| 2013/0064783 A1 | 3/2013 | Baker et al. |
| 2013/0131016 A1 | 5/2013 | Akama et al. |
| 2013/0131017 A1 | 5/2013 | Akama et al. |
| 2013/0165411 A1* | 6/2013 | Gordeev et al. ................ 514/64 |
| 2013/0196433 A1 | 8/2013 | Raines et al. |
| 2013/0210770 A1 | 8/2013 | Baker et al. |
| 2013/0231304 A1 | 9/2013 | Jacobs et al. |
| 2013/0244980 A1 | 9/2013 | Baker et al. |
| 2013/0316979 A1 | 11/2013 | Baker et al. |

FOREIGN PATENT DOCUMENTS

| | | |
|---|---|---|
| AU | 2012327230 A1 | 7/2013 |
| CA | 2190155 A1 | 12/1995 |
| CA | 2635680 A1 | 7/2007 |
| CA | 2642583 A1 | 8/2007 |
| CA | 2680587 A1 | 9/2009 |
| CN | 101505603 | 8/2009 |
| EP | 0765331 B1 | 9/2000 |
| EP | 1444981 A1 | 8/2004 |
| EP | 1980564 A1 | 10/2008 |
| EP | 1765360 B1 | 11/2009 |
| EP | 1765358 B1 | 2/2011 |
| EP | 2343304 A1 | 7/2011 |
| EP | 2564857 A1 | 3/2013 |
| GB | 961280 | 6/1964 |
| GB | 1006336 | 6/1965 |
| GB | 1396904 | 6/1975 |
| WO | 9533754 A1 | 12/1995 |
| WO | 2005087742 A1 | 9/2005 |
| WO | 2006089067 A2 | 8/2006 |
| WO | 2007102604 A2 | 9/2006 |
| WO | 2007071632 A2 | 6/2007 |
| WO | 2007078340 * | 7/2007 |
| WO | 2007078340 A2 | 7/2007 |
| WO | 2007079119 A2 | 7/2007 |
| WO | 2007095638 A2 | 8/2007 |
| WO | 2007131072 A2 | 11/2007 |
| WO | 2007146965 A2 | 12/2007 |
| WO | 2008064345 A2 | 5/2008 |
| WO | 2008070257 A2 | 6/2008 |
| WO | 2008115385 A2 | 9/2008 |
| WO | 2008156798 A1 | 12/2008 |
| WO | 2008157726 A1 | 12/2008 |
| WO | 2009046098 A1 | 4/2009 |
| WO | 2009053741 A2 | 4/2009 |
| WO | 2009111676 A2 | 9/2009 |
| WO | 2009140309 A2 | 11/2009 |
| WO | 2010027975 A1 | 3/2010 |
| WO | 2010028005 A1 | 3/2010 |
| WO | 2010045503 * | 4/2010 |
| WO | 2010045503 A1 | 4/2010 |
| WO | 2010045505 A1 | 4/2010 |
| WO | 2010080558 A1 | 7/2010 |
| WO | 2010136475 A1 | 12/2010 |
| WO | 2011017125 * | 2/2011 |
| WO | 2011017125 A1 | 2/2011 |
| WO | 2011019612 A1 | 2/2011 |
| WO | 2011019616 A1 | 2/2011 |
| WO | 2011019618 * | 2/2011 |
| WO | 2011019618 A1 | 2/2011 |
| WO | 2011022337 * | 2/2011 |
| WO | 2011022337 A1 | 2/2011 |
| WO | 2011037731 * | 3/2011 |
| WO | 2011037731 A1 | 3/2011 |
| WO | 2011043817 * | 4/2011 |
| WO | 2011049971 A1 | 4/2011 |
| WO | 2011060196 * | 5/2011 |
| WO | 2011060196 A1 | 5/2011 |
| WO | 2011060199 * | 5/2011 |
| WO | 2011060199 A1 | 5/2011 |
| WO | 2011063293 A1 | 5/2011 |
| WO | 2011094450 A1 | 8/2011 |
| WO | 2011116348 A1 | 9/2011 |
| WO | 2011150190 A2 | 12/2011 |
| WO | 2012033858 A2 | 3/2012 |
| WO | 2012067663 A1 | 5/2012 |
| WO | 2012069652 A2 | 5/2012 |
| WO | 2012139134 A2 | 10/2012 |
| WO | 2012154213 A1 | 11/2012 |
| WO | 2013033270 A2 | 3/2013 |
| WO | 2013050591 A2 | 4/2013 |
| WO | 2013057740 A2 | 4/2013 |
| WO | 2013058824 A1 | 4/2013 |
| WO | 2013078070 A1 | 5/2013 |
| WO | 2013078071 A1 | 5/2013 |
| WO | 2013093615 * | 6/2013 |
| WO | 2013108024 A1 | 7/2013 |
| WO | 2013110005 A1 | 7/2013 |
| WO | 2013154759 A1 | 10/2013 |

OTHER PUBLICATIONS

Alexander et al., "Imprinted Polymers as Protecting Groups for Regioselective Modification of Polyfunctional Substrates", Journal of American Chemical Society, 1999, pp. 6640-6651, vol. 121, United Kingdom (12 pages).

Haynes et al., "Reactions of Boronophthalide", Noyes Chemical Laboratory, University of Illinois, Nov. 1964, pp. 3233, Urbana, USA (5 pages).

Kumar et al., "Development of Practical Methodologies for the Synthesis of Functionalized Benzoboroxoles", Tetrahendron Letters, Elsevier, Amsterdam, NL, Col. 51, No. 34, Aug. 25, 2010, pp. 4482-4485.

Mao et al., "AN2690, a topical antifungal agent in development for the treatment of onychomycosis represents a new class and has a novel mechanism of action," Anacor Pharmaceuticals Poster #769.

Baker, Stephen J., et al., Discovery of a new boron-containing antifungal agent, 5-fluoro-1, 3-dihydro-1-hydroxy-2,1-benzoxaborate (AN2690), for the potential treatment of onychomycosis, Journal of Medicinal Chemistry, Jul. 1, 2006, pp. 4447-4450, vol. 49(15), American Chemical Society, United States.

International Search Report, PCT/US2014/013510, Dow AgroSciences LLC, Jun. 25, 2014.

\* cited by examiner

Compound A

Compound B 0.125 mg Compound A (benzoxaborole)

0 mg (acetone)

USE OF BENZOXABOROLES AS VOLATILE ANTIMICROBIAL AGENTS ON MEATS, PLANTS, OR PLANT PARTS

CROSS-REFERENCE

This application is a continuation of U.S. patent application Ser. No. 14/167,093, filed Jan. 29, 2014, and claims the benefit of U.S. provisional patent application No. 61/758,313 filed Jan. 30, 2013, each of which is incorporated by reference herein in its entirety.

BACKGROUND OF THE INVENTION

A number of compounds containing an oxaborole ring have been disclosed previously. However, there has been no teaching that these oxaborole compounds are volatile antimicrobial agents. In addition, these oxaborole compounds have not been used in agricultural applications.

Thus, there remains a need to develop new uses of various volatile antimicrobial agents and/or combinations with a volatile plant growth regulator, in particular for agricultural applications.

SUMMARY OF THE INVENTION

This invention is related to the use of a volatile antimicrobial compound against pathogens affecting meats, plants, or plant parts. The volatile antimicrobial compounds provided include certain oxaborole compounds, for example benzoxaboroles. Delivery systems are provided to take advantage of the volatile nature of these antimicrobial compounds. Also combinations with a volatile plant growth regulator, for example 1-methylcyclopropene (1-MCP), are disclosed.

In one aspect, provided is a method of using a volatile antimicrobial compound against pathogens affecting meats, plants, or plant parts. The method comprises contacting the meats, plants, or plant parts with an effective amount of the volatile antimicrobial compound having a structure of formula (I), (II), or (III):

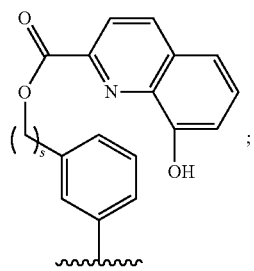

wherein q1 and q2 are independently 1, 2, or 3;

q3=0, 1, 2, 3, or 4;

M is hydrogen, halogen, —OCH$_3$, or —CH$_2$—O—CH$_2$—O—CH$_3$;

M$^1$ is halogen, —CH$_2$OH, or —OCH$_3$;

X is O, S, or NR$^{1c}$, wherein R$^{1c}$ is hydrogen, substituted alkyl, or unsubstituted alkyl;

R$^1$, R$^{1a}$, R$^{1b}$, R$^2$, and R$^5$ are independently hydrogen, OH, NH$_2$, SH, CN, NO$_2$, SO$_2$, OSO$_2$OH, OSO$_2$NH$_2$, substituted or unsubstituted cycloalkyl, substituted or unsubstituted heterocycloalkyl, substituted or unsubstituted aryl, or substituted or unsubstituted heteroaryl;

R* is substituted or unsubstituted aryl, substituted or unsubstituted arylalkyl, substituted or unsubstituted heteroaryl, substituted or unsubstituted heteroarylalkyl, or substituted or unsubstituted vinyl;

with a proviso that when M is F, R* is not a member selected from:

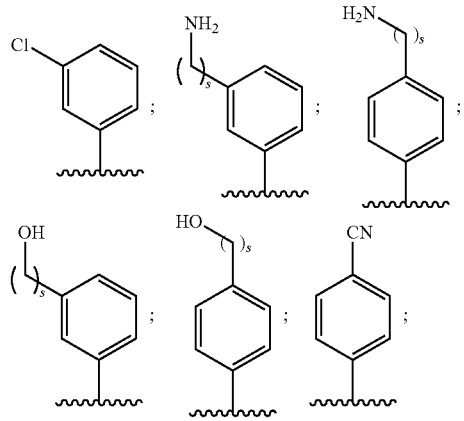

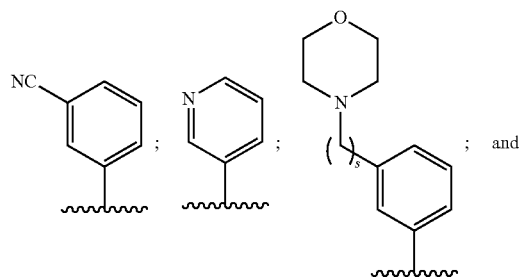

and with a proviso that when M is Cl, R* is not a member selected from:

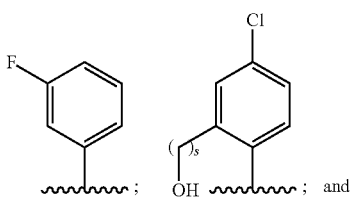

and

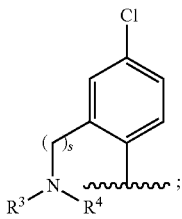

and with a proviso that when M is hydrogen, R* is not a member selected from:

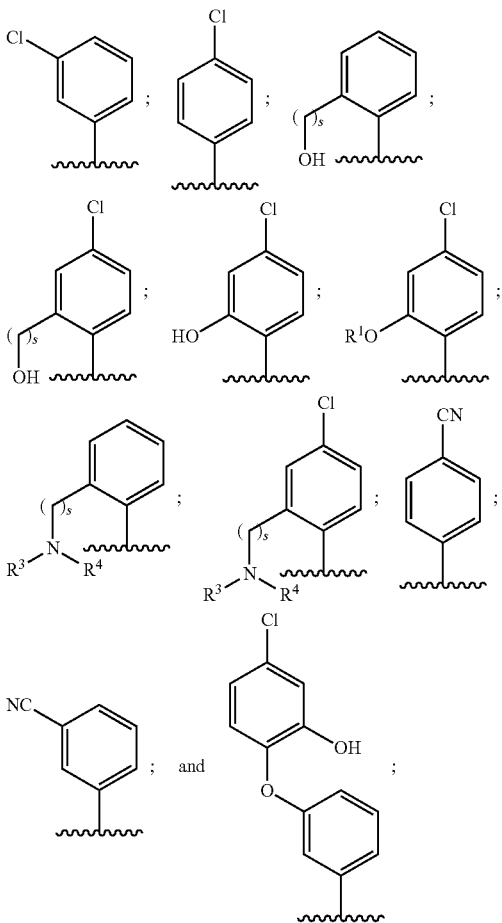

wherein s=1 or 2; and $R^3$ and $R^4$ are independently methyl or ethyl;

and with a provision that when M is $OCH_3$, R* is not a member selected from:

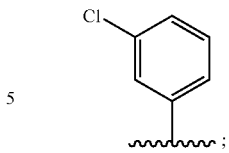

and with a provision that when $M^1$ is F, R* is not a member selected from:

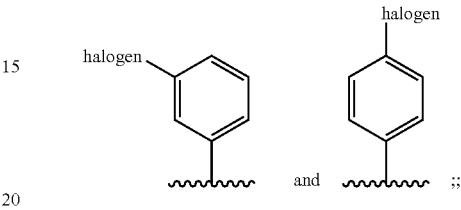

and agriculturally acceptable salts thereof.

In one embodiment of the method provided, the pathogen is selected from the group consisting of *Alternaria* spp., *Aspergillus* spp., *Botryospheria* spp., *Botrytis* spp., *Byssochlamys* spp., *Colletotrichum* spp., *Diplodia* spp., *Fusarium* spp., *Geotrichum* spp., *Lasiodiplodia* spp., *Monolinia* spp., *Mucor* spp., *Penicillium* spp., *Pezicula* spp., *Phomopsis* spp., *Phytophthora* spp., *Pythium* spp., *Rhizoctonia* spp., *Rhizopus* spp., *Sclerotinia* spp., and *Venturia* spp. In another embodiment, the pathogen is selected from the group consisting of *Erwinia* spp., *Pectobacterium* spp., *Pseudomonas* spp., *Ralstonia* spp., *Xanthomonas* spp., *Salmonella* spp., *Escherichia* spp., *Listeria* spp., *Bacillus* spp., *Shigella* spp., and *Staphylococcus* spp. In another embodiment, the pathogen is selected from the group consisting of *Candida* spp., *Debaryomyces* spp., *Bacillus* spp., *Campylobacter* spp., *Clostridium* spp., *Cryptosporidium* spp., *Giardia* spp., *Vibrio* spp., and *Yersinia* spp. In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during palletization, in-box treatment, treatment during transportation, and treatment during storage and/or throughout the distribution network.

In another embodiment, the plants or plant parts comprise transgenic plants or transgenic plant parts. In another embodiment, the plants or plant parts are selected from the group consisting of corn, wheat, cotton, rice, soybean, and canola. In another embodiment, the plants or plant parts are selected from the group consisting of fruit, vegetables, nursery, turf and ornamental crops. In a further embodiment, the fruit is selected from the group consisting of banana, pineapple, citrus including oranges, lemon, lime, grapefruit, and other citrus, grapes, watermelon, cantaloupe, muskmelon, and other melons, apple, peach, pear, cherry, kiwifruit, mango, nectarine, guava, papaya, persimmon, pomegranate, avocado, fig, and berries including strawberry, blueberry, raspberry, blackberry, currants and other types of berries. In a further embodiment, the vegetable is selected from the group consisting of tomato, potato, sweet potato, cassava, pepper, bell pepper, carrot, celery, squash, eggplant, cabbage, cauliflower, broccoli, asparagus, mushroom, onion, garlic, leek, and snap bean. A further embodiment, the flower or flower part is selected from the group consisting of roses, carnations, orchids, geraniums, lily or other ornamental flowers. A further embodiment, the meat is selected from the group of beef, bison, chicken, deer, goat, turkey, pork, sheep, fish, shellfish, mollusks, or dry-cured meat products.

In one embodiment, the contacting comprises applying the volatile antimicrobial compound by ways selected from the group consisting of spray, mist, thermal or non-thermal fogging, drench, gas treatment, and combinations thereof. In a further embodiment, the gas treatment is selected from the group consisting of release from a sachet, release from a synthetic or natural film, fibrous material, and/or release from liner or other packaging materials, release from powder, release from a gas-releasing generator, release using a compressed or non-compressed gas cylinder, release from a droplet inside a box, and combinations thereof. In another embodiment, the method further comprises contacting the meats, plants, plant parts with a volatile plant growth regulator. In a further embodiment, the volatile plant growth regulator is a cyclopropene compound. In a further embodiment, the cyclopropene compound comprises 1-methylcyclopropene (1-MCP).

In another aspect, provided is a method of using a volatile antimicrobial compound against pathogens affecting meats, plants, or plant parts. The method comprises contacting the meats, plants, or plant parts with an effective amount of the volatile antimicrobial compound of formula (IV):

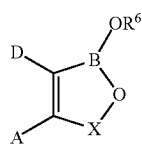

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and $R^6$ is hydrogen, $C_1$-$C_{18}$-alkyl, ($C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

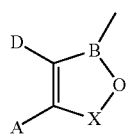

(V)

wherein A, D and X are as defined herein except for boronophthalide;

and agriculturally acceptable salts thereof.

In one embodiment of the method provided, the pathogen is selected from the group consisting of *Alternaria* spp., *Aspergillus* spp., *Botryospheria* spp., *Botrytis* spp., *Byssochlamys* spp., *Colletotrichum* spp., *Diplodia* spp., *Fusarium* spp., *Geotrichum* spp., *Lasiodiplodia* spp., *Monolinia* spp., *Mucor* spp., *Penicillium* spp., *Pezicula* spp., *Phomopsis* spp., *Phytophthora* spp., *Pythium* spp., *Rhizoctonia* spp., *Rhizopus* spp., *Sclerotinia* spp., and *Venturia* spp. In another embodiment, the pathogen is selected from the group consisting of *Erwinia* spp., *Pectobacterium* spp., *Pseudomonas* spp., *Ralstonia* spp., *Xanthomonas* spp.; *Salmonella* spp., *Escherichia* spp., *Listeria* spp., *Bacillus* spp., *Shigella* spp., and *Staphylococcus* spp. In another embodiment, the pathogen is selected from the group consisting of *Candida* spp., *Debaryomyces* spp., *Bacillus* spp., *Campylobacter* spp., *Clostridium* spp., *Cryptosporidium* spp., *Giardia* spp., *Vibrio* spp., and *Yersinia* spp. In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during palletization, in-box treatment, treatment during transportation, and treatment during storage and/or throughout the distribution network.

In another embodiment, the plants or plant parts comprise transgenic plants or transgenic plant parts. In another embodiment, the plants or plant parts are selected from the group consisting of corn, wheat, cotton, rice, soybean, and canola. In another embodiment, the plants or plant parts are selected from the group consisting of fruit, vegetables, nursery, turf and ornamental crops. In a further embodiment, the fruit is selected from the group consisting of banana, pineapple, citrus including oranges, lemon, lime, grapefruit, and other citrus, grapes, watermelon, cantaloupe, muskmelon, and other melons, apple, peach, pear, cherry, kiwifruit, mango, nectarine, guava, papaya, persimmon, pomegranate, avocado, fig, and berries including strawberry, blueberry, raspberry, blackberry, currants and other types of berries. In a further embodiment, the vegetable is selected from the group consisting of tomato, potato, sweet potato, cassava, pepper, bell pepper, carrot, celery, squash, eggplant, cabbage, cauliflower, broccoli, asparagus, mushroom, onion, garlic, leek, and snap bean. A further embodiment, the flower or flower part is selected from the group consisting of roses, carnations, orchids, geraniums, lily or other ornamental flowers. A further embodiment, the meat is selected from the group of beef, bison, chicken, deer, goat, turkey, pork, sheep, fish, shellfish, mollusks, or dry-cured meat products.

In one embodiment, the contacting comprises applying the volatile antimicrobial compound by ways selected from the group consisting of spray, mist, thermal or non-thermal fogging, drench, gas treatment, and combinations thereof. In a further embodiment, the gas treatment is selected from the group consisting of release from a sachet, release from a synthetic or natural film, fibrous material, and/or release from a liner or other packaging materials, release from powder, release from a gas-releasing generator, release using a compressed or non-compressed gas cylinder, release from a droplet inside a box, and combinations thereof. In another embodiment, the method further comprises contacting the meats, plants, or plant parts with a volatile plant growth regulator. In a further embodiment, the volatile plant growth regulator is a cyclopropene compound. In a further embodiment, the cyclopropene compound comprises 1-methylcyclopropene (1-MCP).

In another aspect, provided is a method of using a volatile antimicrobial compound against pathogens affecting meats, plants, or plant parts. The method comprises contacting the meats, plants, or plant parts with an effective amount of the volatile antimicrobial compound of formula (VI):

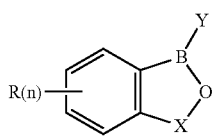

(VI)

wherein each R is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;

B is boron;

X=(CR$_2$)$_m$ where m=1, 2, 3, or 4;

Y is alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

with a proviso that R is not aryloxy or heteroaryloxy when Y is hydroxyl;

and agriculturally acceptable salts thereof.

In one embodiment, the volatile antimicrobial compound has a structure of formula (VII):

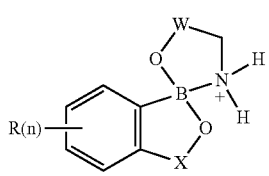

(VII)

wherein W=(CH$_2$)$_q$ where q is 1, 2, or 3.

In another embodiment, the volatile antimicrobial compound has a structure of

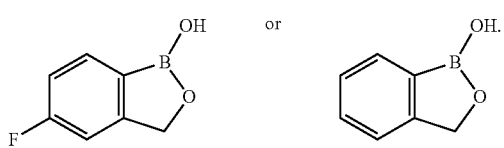 [SMILES: OB1OCc2cc(F)ccc21 ; "or" ; OB1OCc2ccccc21]

In one embodiment of the method provided, the pathogen is selected from the group consisting of *Alternaria* spp., *Aspergillus* spp., *Botryospheria* spp., *Botrytis* spp., *Byssochlamys* spp., *Colletotrichum* spp., *Diplodia* spp., *Fusarium* spp., *Geotrichum* spp., *Lasiodiplodia* spp., *Monolinia* spp., *Mucor* spp., *Penicillium* spp., *Pezicula* spp., *Phomopsis* spp., *Phytophthora* spp., *Pythium* spp., *Rhizoctonia* spp., *Rhizopus* spp., *Sclerotinia* spp., and *Venturia* spp. In another embodiment, the pathogen is selected from the group consisting of *Erwinia* spp., *Pectobacterium* spp., *Pseudomonas* spp., *Ralstonia* spp., *Xanthomonas* spp., *Salmonella* spp., *Escherichia* spp., *Listeria* spp., *Bacillus* spp., *Shigella* spp., and *Staphylococcus* spp. In another embodiment, the pathogen is selected from the group consisting of *Candida* spp., *Debaryomyces* spp., *Bacillus* spp., *Campylobacter* spp., *Clostridium* spp., *Cryptosporidium* spp., *Giardia* spp., *Vibrio* spp., and *Yersinia* spp. In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during palletization, in-box treatment, treatment during transportation, and treatment during storage and/or throughout the distribution network.

In another embodiment, the plants or plant parts comprise transgenic plants or transgenic plant parts. In another embodiment, the plants or plant parts are selected from the group consisting of corn, wheat, cotton, rice, soybean, and canola. In another embodiment, the plants or plant parts are selected from the group consisting of fruit, vegetables, nursery, turf and ornamental crops. In a further embodiment, the fruit is selected from the group consisting of banana, pineapple, citrus including oranges, lemon, lime, grapefruit, and other citrus, grapes, watermelon, cantaloupe, muskmelon, and other melons, apple, peach, pear, cherry, kiwifruit, mango, nectarine, guava, papaya, persimmon, pomegranate, avocado, fig, and berries including strawberry, blueberry, raspberry, blackberry, currants and other types of berries. In a further embodiment, the vegetable is selected from the group consisting of tomato, potato, sweet potato, cassava, pepper, bell pepper, carrot, celery, squash, eggplant, cabbage, cauliflower, broccoli, asparagus, mushroom, onion, garlic, leek, and snap bean. A further embodiment, the flower or flower part is selected from the group consisting of roses, carnations, orchids, geraniums, lily or other ornamental flowers. A further embodiment, the meat is selected from the group of beef, bison, chicken, deer, goat, turkey, pork, sheep, fish, shellfish, mollusks, or dry-cured meat products.

In one embodiment, the contacting comprises applying the volatile antimicrobial compound by ways selected from the group consisting of spray, mist, thermal or non-thermal fogging, drench, gas treatment, and combinations thereof. In a further embodiment, the gas treatment is selected from the group consisting of release from a sachet, release from a synthetic or natural film, fibrous material, and/or release from liner or other packaging materials, release from powder, release from a gas-releasing generator, release using a compressed or non-compressed gas cylinder, release from a droplet inside a box, and combinations thereof. In another embodiment, the method further comprises contacting the meats, plants, plant parts with a volatile plant growth regulator. In a further embodiment, the volatile plant growth regulator is a cyclopropene compound. In a further embodiment, the cyclopropene compound comprises 1-methylcyclopropene (1-MCP).

In another aspect, provided is a method of using a volatile antimicrobial compound against pathogens affecting meats, plants, or plant parts. The method comprises contacting the meats, plants, or plant parts with an effective amount of the volatile antimicrobial compound of formula (VIII):

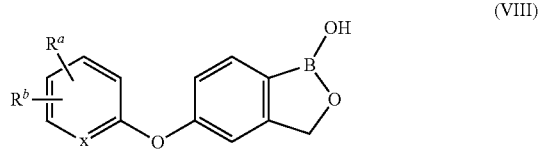

(VIII)

wherein $R^a$ is CN, C(O)NR$^9$R$^{10}$, or C(O)OR$^{11}$ wherein $R^{11}$ is hydrogen, substituted alkyl, or unsubstituted alkyl, X is N, CH and CR$^b$;

$R^b$ is halogen, substituted or unsubstituted alkyl, C(O)R$^{12}$, C(O)OR$^{12}$, OR$^{12}$, NR$^{12}$R$^{13}$, wherein R$^9$, R$^{10}$, R$^{12}$, and R$^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

with a proviso that R$^9$ and R$^{10}$, together with the atoms to which they are attached, are optionally combined to form a 4- to 8-membered substituted or unsubstituted heterocycloalkyl ring;

and with a proviso that R$^{12}$ and R$^{13}$, together with the atoms to which they are attached, are optionally combined to form a 4- to 8-membered substituted or unsubstituted heterocycloalkyl ring;

and agriculturally acceptable salts thereof.

In one embodiment of the method provided, the pathogen is selected from the group consisting of *Alternaria* spp., *Aspergillus* spp., *Botryospheria* spp., *Botrytis* spp., *Byssochlamys* spp., *Colletotrichum* spp., *Diplodia* spp., *Fusarium* spp., *Geotrichum* spp., *Lasiodiplodia* spp., *Monolinia* spp., *Mucor* spp., *Penicillium* spp., *Pezicula* spp., *Phomopsis* spp., *Phytophthora* spp., *Pythium* spp., *Rhizoctonia* spp., *Rhizopus* spp., *Sclerotinia* spp., and *Venturia* spp. In another embodiment, the pathogen is selected from the group consisting of *Erwinia* spp., *Pectobacterium* spp., *Pseudomonas* spp., *Ralstonia* spp., *Xanthomonas* spp., *Salmonella* spp., *Escherichia* spp., *Listeria* spp., *Bacillus* spp., *Shigella* spp., and *Staphylococcus* spp. In another embodiment, the pathogen is selected from the group consisting of *Candida* spp., *Debaryomyces* spp., *Bacillus* spp., *Campylobacter* spp., *Clostridium* spp., *Cryptosporidium* spp., *Giardia* spp., *Vibrio* spp., and *Yersinia* spp. In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during palletization, in-box treatment, treatment during transportation, and treatment during storage and/or throughout the distribution network.

In another embodiment, the plants or plant parts comprise transgenic plants or transgenic plant parts. In another embodiment, the plants or plant parts are selected from the group consisting of corn, wheat, cotton, rice, soybean, and canola. In another embodiment, the plants or plant parts are selected from the group consisting of fruit, vegetables, nursery, turf and ornamental crops. In a further embodiment, the fruit is selected from the group consisting of banana, pineapple, citrus including oranges, lemon, lime, grapefruit, and other citrus, grapes, watermelon, cantaloupe, muskmelon, and other melons, apple, peach, pear, cherry, kiwifruit, mango, nectarine, guava, papaya, persimmon, pomegranate, avocado, fig, and berries including strawberry, blueberry, raspberry, blackberry, currants and other types of berries. In a further embodiment, the vegetable is selected from the group consisting of tomato, potato, sweet potato, cassava, pepper, bell pepper, carrot, celery, squash, eggplant, cabbage, cauliflower, broccoli, asparagus, mushroom, onion, garlic, leek, and snap bean. A further embodiment, the flower or flower part is selected from the group consisting of roses, carnations, orchids, geraniums, lily or other ornamental flowers. A further embodiment, the meat is selected from the group of beef, bison, chicken, deer, goat, turkey, pork, sheep, fish, shellfish, mollusks, or dry-cured meat products.

In one embodiment, the contacting comprises applying the volatile antimicrobial compound by ways selected from the group consisting of spray, mist, thermal or non-thermal fogging, drench, gas treatment, and combinations thereof. In a further embodiment, the gas treatment is selected from the group consisting of release from a sachet, release from a synthetic or natural film, release from liner or other packaging materials, release from powder, release from a gas-releasing generator, release using a compressed or non-compressed gas cylinder, release from a droplet inside a box, and combinations thereof. In another embodiment, the method further comprises contacting the meats, plants, plant parts with a volatile plant growth regulator. In a further embodiment, the volatile plant growth regulator is a cyclopropene compound. In a further embodiment, the cyclopropene compound comprises 1-methylcyclopropene (1-MCP).

BRIEF DESCRIPTION OF THE DRAWINGS

FIG. 4A shows a grape sample not inoculated with *Botrytis cinerea*.

FIG. 4B shows an inoculated grape sample treated with 0.04 mg of Compound A after the 14 day bioassay test described in Example 4.

FIG. 4C shows an inoculated grape sample treated with 0.0024 mg of Compound A after the 14 day bioassay test.

FIG. 4D shows an inoculated grape sample treated with pure acetone, including no Compound A, after the 14 day bioassay test.

FIG. 5A shows a representative photo of exemplary in vivo inhibition of *Botrytis cinerea* by a volatile application of Compound A after a 3-day treatment at 21° C., followed by an additional 2 days at 21° C., as described in Example 6.

FIG. 5B shows an inoculated strawberry sample treated with pure acetone, including no Compound A, after the 3-day treatment at 21° C., followed by an additional 2 days at 21° C.

DETAILED DESCRIPTION OF THE INVENTION

Figure 1:
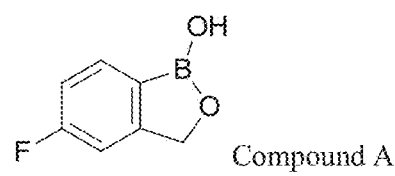
FIG. 1 shows the chemical structure of an exemplary Compound A of the invention.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg, *Advanced Organic Chemistry* 4$^{th}$ Ed., Vols. A (2000) and B (2001), Plenum Press, New York, N.Y.

As used herein, the phrase "moiety" refers to a specific segment or functional group of a molecule. Chemical moieties are often recognized chemical entities embedded in or appended to a molecule.

As used herein, the phrases "heteroatom" and "hetero-" refer to atoms other than carbon (C) and hydrogen (H). Examples of heteroatoms include oxygen (O), nitrogen (N) sulfur (S), silicon (Si), germanium (Ge), aluminum (Al) and boron (B).

As used herein, the phrases "halo" and "halogen" are interchangeable and refer to fluoro (—F), chloro (—Cl), bromo (—Br), and iodo (—I).

As used herein, the phrase "alkyl" refers to an unsubstituted or substituted, hydrocarbon group and can include straight, branched, cyclic, saturated and/or unsaturated features. Although the alkyl moiety may be an "unsaturated alkyl" moiety, which means that it contains at least one alkene or alkyne moiety, typically, the alkyl moiety is a "saturated alkyl" group, which means that it does not contain any alkene or alkyne moieties. Likewise, although the alkyl moiety may be cyclic, the alkyl moiety typically is acyclic group. Thus, in some embodiments, "alkyl" refers to an optionally substituted straight-chain, or optionally substituted branched-chain saturated hydrocarbon monoradical having from about one to about thirty carbon atoms in some embodiments, from about one to about fifteen carbon atoms in some embodiments, and from about one to about six carbon atoms in further embodiments. Examples of saturated alkyl radicals include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, tert-butyl, n-pentyl, isopentyl, neopentyl, and n-hexyl, and longer alkyl groups, such as heptyl, and octyl. It should be noted that whenever it appears herein, a numerical range such as "1 to 6" refers to each integer in the given range; e.g., "1 to 6 carbon atoms" or "$C_{1-6}$" or "$C_1$-$C_6$" means that the alkyl group may consist of 1 carbon atom, 2 carbon atoms, 3 carbon atoms, 4 carbon atoms, 5 carbon atoms, and/or 6 carbon atoms, although the present definition also covers the occurrence of the term "alkyl" where no numerical range is designated.

As used herein, the phrase "substituted alkyl" refers to an alkyl group, as defined herein, in which one or more (up to about five, preferably up to about three) hydrogen atoms is replaced by a substituent independently selected from the substituent group defined herein.

As used herein, the phrases "substituents" and "substituted" refer to groups which may be used to replace another group on a molecule. Such groups are known to those of skill in the chemical arts and may include, without limitation, one or more of the following independently selected groups, or designated subsets thereof: halogen, —CN, —OH, —NO$_2$, —N$_3$, =O, =S, =NH, —SO$_2$, —NH$_2$, —COOH, nitroalkyl, amino, including mono- and di-substituted amino groups, cyanato, isocyanato, thiocyanato, isothiocyanato, guanidinyl, O-carbamyl, N-carbamyl, thiocarbamyl, uryl, isouryl, thiouryl, isothiouryl, mercapto, sulfanyl, sulfinyl, sulfonyl, sulfonamidyl, phosphonyl, phosphatidyl, phosphoramidyl, dialkylamino, diarylamino, diarylalkylamino; and the protected compounds thereof. The protecting groups that may form the protected compounds of the above substituents are known to those of skill in the art and may be found in references such as Greene and Wuts, *Protective Groups in Organic Synthesis,* 3rd ed.; John Wiley & Sons, New York, N.Y. (1999) and Kocienski, *Protective Groups*; Thieme Verlag, New York, N.Y. (1994) which are incorporated herein by reference in their entirety.

As used herein, the phrase "alkoxy" refers to the group —O-alkyl, where alkyl is as defined herein. In one embodiment, alkoxy groups include, e.g., methoxy, ethoxy, n-propoxy, isopropoxy, n-butoxy, tert-butoxy, sec-butoxy, n-pentoxy, n-hexoxy, 1,2-dimethylbutoxy, and the like. The alkoxy can be unsubstituted or substituted.

As used herein, the phrases "cyclic" and "membered ring" refer to any cyclic structure, including alicyclic, heterocyclic, aromatic, heteroaromatic and polycyclic fused or non-fused ring systems as described herein. The term "membered" is meant to denote the number of skeletal atoms that constitute the ring. Thus, for example, pyridine, pyran, and pyrimidine are six-membered rings and pyrrole, tetrahydrofuran, and thiophene are five-membered rings.

As used herein, the phrase "aromatic" refers to a cyclic or polycyclic moiety having a conjugated unsaturated (4n+2)π electron system (where n is a positive integer), sometimes referred to as a delocalized π electron system.

As used herein, the phrase "aryl" refers to an optionally substituted, aromatic, cyclic, hydrocarbon monoradical of from six to about twenty ring atoms, preferably from six to about ten carbon atoms and includes fused (or condensed) and non-fused aromatic rings. A fused aromatic ring radical contains from two to four fused rings where the ring of attachment is an aromatic ring, and the other individual rings within the fused ring may be cycloalkyl, cycloalkenyl, cycloalkynyl, heterocycloalkyl, heterocycloalkenyl, heterocycloalkynyl, aromatic, heteroaromatic or any combination thereof. A non-limiting example of a single ring aryl group includes phenyl; a fused ring aryl group includes naphthyl, anthryl, azulenyl; and a non-fused bi-aryl group includes biphenyl.

As used herein, the phrase "substituted aryl" refers to an aryl group, as defined herein, in which one or more (up to about five, preferably up to about three) hydrogen atoms is replaced by a substituent independently selected from the group defined herein, (except as otherwise constrained by the definition for the aryl substituent).

As used herein, the phrase "heteroaryl" refers to an optionally substituted, aromatic, cyclic monoradical containing from about five to about twenty skeletal ring atoms, preferably from five to about ten ring atoms and includes fused (or condensed) and non-fused aromatic rings, and which have one or more (one to ten, preferably about one to about four) ring atoms selected from an atom other than carbon (i.e., a heteroatom) such as, for example, oxygen, nitrogen, sulfur, selenium, phosphorus or combinations thereof. The term heteroaryl includes optionally substituted fused and non-fused heteroaryl radicals having at least one heteroatom. A fused heteroaryl radical may contain from two to four fused rings where the ring of attachment is a heteroaromatic ring and the other individual rings within the fused ring system may be alicyclic, heterocyclic, aromatic, heteroaromatic or any combination thereof. The term heteroaryl also includes fused and non-fused heteroaryls having from five to about twelve skeletal ring atoms, as well as those having from five to about ten skeletal ring atoms. Examples of heteroaryl groups include, but are not limited to, acridinyl, benzo[1,3]dioxole, benzimidazolyl, benzindazolyl, benzoisooxazolyl, benzokisazolyl, benzofuranyl, benzofurazanyl, benzopyranyl, benzothiadiazolyl, benzothiazolyl, benzo[b]thienyl, benzothiophenyl, benzothiopyranyl, benzotriazolyl, benzoxazolyl, carbazolyl, carbolinyl, chromenyl, cinnolinyl, furanyl, furazanyl, furopyridinyl, furyl, imidazolyl, indazolyl, indolyl, indolidinyl, indolizinyl, isobenzofuranyl, isoindolyl, isoxazolyl, isoquinolinyl, isothiazolyl, naphthylidinyl, naphthyridinyl, oxadiazolyl, oxazolyl, phenoxazinyl, phenothiazinyl, phenazinyl, phenoxathiynyl, thianthrenyl, phenathridinyl, phenathrolinyl, phthalazinyl, pteridinyl, purinyl, puteridinyl, pyrazyl, pyrazolyl, pyridyl, pyridinyl, pyridazinyl, pyrazinyl, pyrimidinyl, pyrimidyl, pyrrolyl, quinazolinyl, quinolinyl, quinoxalinyl, tetrazolyl, thiadiazolyl, thiazolyl, thienyl, triazinyl, (1,2,3,)- and (1,2,4)-triazolyl and the like, and their oxides where appropriate, such as for example pyridyl-N-oxide.

As used herein, the phrase "substituted heteroaryl" refers to a heteroaryl group, as defined herein, in which one or more (up to about five, preferably up to about three) hydrogen atoms is replaced by a substituent independently selected from the group defined herein.

As used herein, the phrase "leaving group" refers to a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like. In some embodiments, a leaving group can be HC(O)—COOH or RC(O)—COOH, wherein R is a $C_1$-$C_6$ alkyl or substituted $C_1$-$C_6$ alkyl.

The compounds of the invention as described herein may be synthesized using standard synthetic techniques known to those of skill in the art or using methods known in the art in combination with methods described herein. The starting materials used for the synthesis of the compounds of the invention as described herein, can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, *Advanced Organic Chemistry* 4th Ed. (1992) John Wiley & Sons, New York, N.Y.; Carey and Sundberg, *Advanced Organic Chemistry* 4th Ed., Vols. A (2000) and B (2001) Plenum Press, New York, N.Y. and Greene and Wuts, *Protective Groups in Organic Synthesis*, 3rd Ed. (1999) John Wiley & Sons, New York, N.Y., (all of which are incorporated by reference in their entirety). General methods for the preparation of compounds as disclosed herein may be derived from known reactions in the field, and the reactions may be modified by the use of appropriate reagents and conditions, as would be recognized by the skilled person, for the introduction of the various moieties found in the formulae as provided herein. For example, the compounds described herein can be modified using various electrophiles or nucleophiles to form new functional groups or substituents.

In some embodiments, the volatile antimicrobial compound of the invention has a structure of formula (I), (II), or (III):

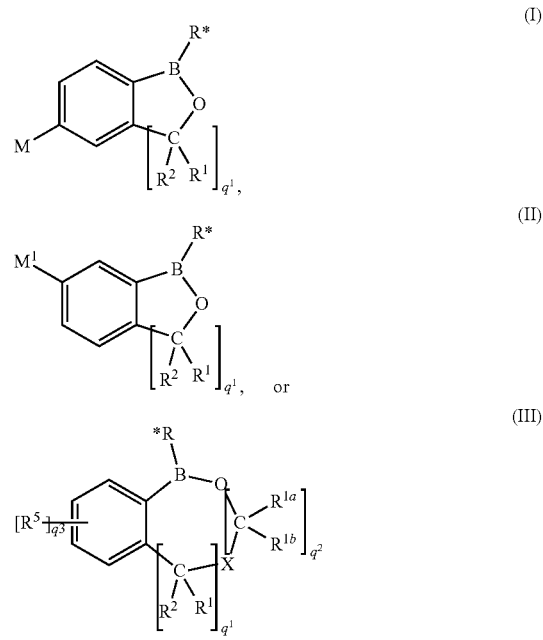

wherein q1 and q2 are independently 1, 2, or 3;
q3=0, 1, 2, 3, or 4;
M is hydrogen, halogen, —$OCH_3$, or —$CH_2$—O—$CH_2$—O—$CH_3$;
$M^1$ is halogen, —$CH_2OH$, or —$OCH_3$;
X is O, S, or $NR^{1c}$, wherein $R^{1c}$ is hydrogen, substituted alkyl, or unsubstituted alkyl;
$R^1$, $R^{1a}$, $R^{1b}$, $R^2$, and $R^5$ are independently hydrogen, OH, $NH_2$, SH, CN, $NO_2$, $SO_2$, $OSO_2OH$, $OSO_2NH_2$, substituted or unsubstituted cycloalkyl, substituted or unsubstituted heterocycloalkyl, substituted or unsubstituted aryl, or substituted or unsubstituted heteroaryl;
R* is substituted or unsubstituted aryl, substituted or unsubstituted arylalkyl, substituted or unsubstituted heteroaryl, substituted or unsubstituted heteroarylalkyl, or substituted or unsubstituted vinyl;
with a proviso that when M is F, R* is not a member selected from:

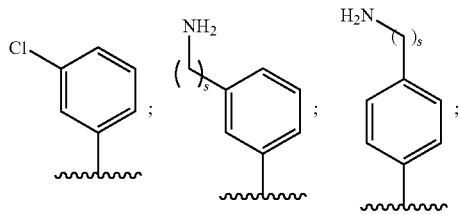

-continued

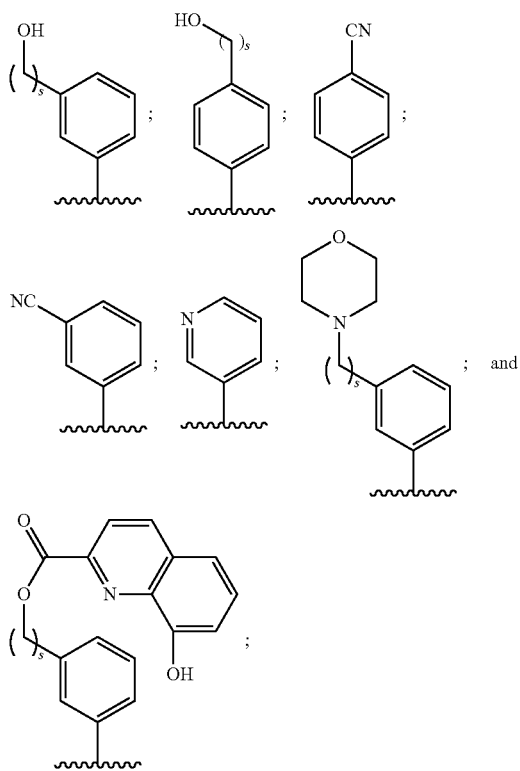

and with a proviso that when M is Cl, R* is not a member selected from:

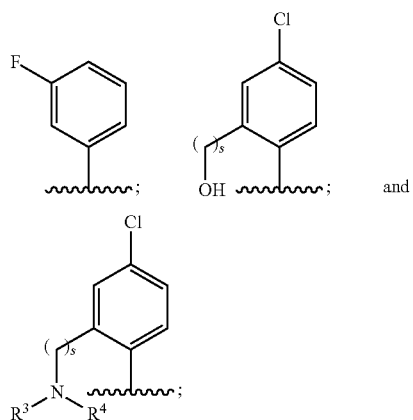

and with a proviso that when M is hydrogen, R* is not a member selected from:

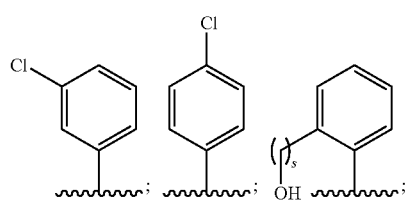

-continued

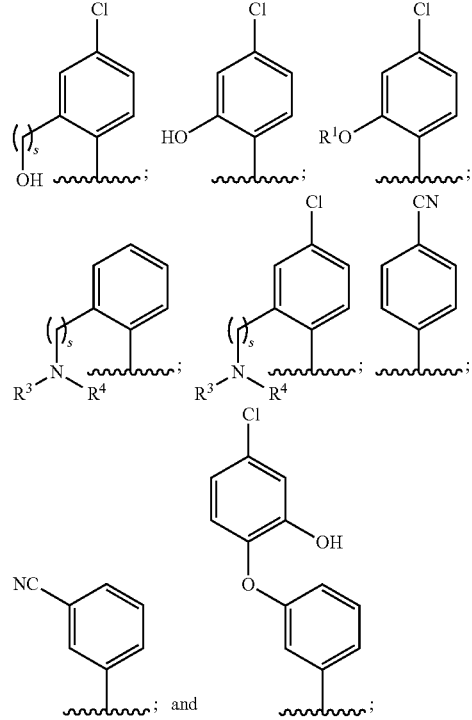

wherein s=1 or 2; and $R^3$ and $R^4$ are independently methyl or ethyl;

and with a provision that when M is $OCH_3$, R* is not a member selected from:

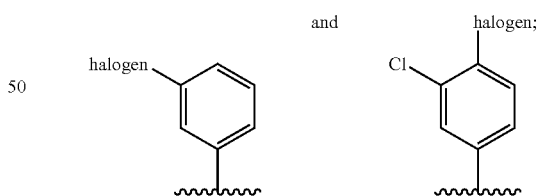

and with a provision that when $M^1$ is F, R* is not a member selected from:

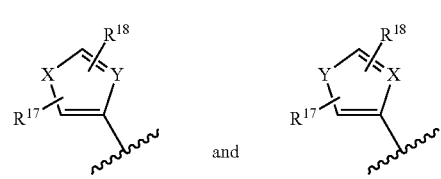

and agriculturally acceptable salts thereof.

In one embodiment, the R* has a structure selected from:

wherein X is a member selected from CH=CH, N=CH, $NR^{14}$, O and S;

wherein $R^{14}$ is a member selected from H, substituted or unsubstituted alkyl, substituted or unsubstituted aryl and substituted or unsubstituted arylalkyl;

Y is a member selected from CH and N;

$R^{17}$ and $R^{18}$ are members independently selected from H, substituted or unsubstituted alkyl, substituted or unsubstituted aryl, substituted or unsubstituted arylalkyl, $(CH_2)_vOH$, $(CH_2)_wNR^{15}R^{16}$, $CO_2H$, $CO_2$-alkyl, $CONH_2$, S-alkyl, S-aryl, SO-alkyl, SO-aryl, $SO_2$-alkyl, $SO_2$-aryl, $SO_2H$, $SCF_2$, CN, halogen, $CF_3$ and $NO_2$;

wherein $R^{15}$ and $R^{16}$ are members independently selected from hydrogen, substituted or unsubstituted alkyl and substituted or unsubstituted alkanoyl;

v=1, 2, or 3; and w=0, 1, 2, or 3.

In another embodiment, the R* has the following structure:

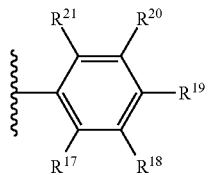

wherein $R^{17}$, $R^{18}$, $R^{19}$, $R^{20}$, and $R^{21}$ are independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_tOH$, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_2H$, $SCF_3$, CN, halogen, $CF_3$, $NO_2$, $(CH_2)—NR^{22}R^{23}$, $SO_2NH_2$, $OCH_2CH_2NH_2$, $OCH_2CH_2NH$-alkyl and $OCH_2CH_2N(alkyl)_2$;

wherein t=1, 2 or 3;

u=0, 1, or 2;

$R^{22}$ and $R^{23}$ are independently selected from H, substituted or unsubstituted alkyl, and substituted or unsubstituted alkanoyl.

In another embodiment, the R* has the following structure:

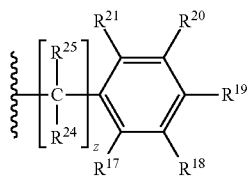

wherein $R^{17}$, $R^{18}$, $R^{19}$, $R^{20}$, and $R^{21}$ are independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_tOH$, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_2H$, $SCF_3$, CN, halogen, $CF_3$, $NO_2$, $(CH_2)_uNR^{22}R^{23}$, $SO_2NH_2$, $OCH_2CH_2NH_2$, $OCH_2CH_2NH$-alkyl and $OCH_2CH_2N(alkyl)_2$;

wherein t=1, 2 or 3;

u=0, 1, or 2;

$R^{22}$ and $R^{23}$ are independently selected from H, substituted or unsubstituted alkyl, and substituted or unsubstituted alkanoyl;

$R^{24}$ and $R^{25}$ are independently selected from H, substituted or unsubstituted alkyl, substituted or unsubstituted aryl, substituted or unsubstituted arylalkyl, substituted or unsubstituted alkyloxy, substituted or unsubstituted aryloxy, substituted or unsubstituted oxazolidin-2-yl, $(CH_2)_t$, OH, $CO_2H$, $CO_2$-alkyl, $CONH_2$, CONH-alkyl, $CON(alkyl)_2$, OH, SH, S-alkyl, S-aryl, SO-alkyl, SO-aryl, $SO_2$-alkyl, $SO_2$-aryl, $SO_3H$, $SCF_3$, CN, halogen, $CF_3$, $NO_2$, $(CH_2)_u NR^{22}R^{23}$, $SO_2NH_2$, $OCH_2CH_2NH_2$, $OCH_2CH_2NH$-alkyl and $OCH_2CH_2N(alkyl)_2$;

Z=1, 2, 3, 4, 5, or 6.

Additional antimicrobial compounds are also disclosed previously in U.S. Pat. No. 8,106,031, and International Patent Application WO 2007/131072A2, the contents of which are hereby incorporated by reference in their entireties.

In some embodiments, the volatile antimicrobial compound of the invention has the structure of formula (IV):

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and $R^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

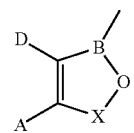

(V)

wherein A, D and X are as defined herein before except for boronophthalide;

and agriculturally acceptable salts thereof.

In one embodiment, the volatile antimicrobial compound of the invention has the structure of formula (IX):

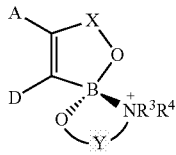
(IX)

wherein A, D, and X are defined as above;

Y is a divalent alkylene linking group containing up to 18 carbon atoms or a divalent alkylene linking group containing up to 18 carbon atoms which is substituted by phenyl, $C_1$-$C_6$ alkoxy, $C_1$-$C_6$-alkylthio; carbonyl alkylene amino; and $R^3$ and $R^4$ are each, independently, hydrogen, $C_1$-$C_{18}$-alkyl or phenyl or $R^3$ together with Y or part of Y forms a 5-, 6- or 7-membered ring containing the nitrogen atom.

In another embodiment, the volatile antimicrobial compound of the invention has the structure of formula (X):

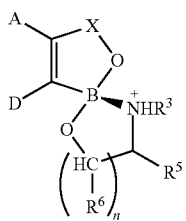
(X)

wherein A, D, and X are defined as above;
n is 1, 2, or 3;
$R^3$ is hydrogen, $C_1$-$C_{18}$-alkyl or phenyl; and
$R^5$ and $R^6$ are each, independently, hydrogen, alkyl containing up to a total of 16 carbon atoms or phenyl.

Additional antimicrobial compounds are also disclosed previously in U.S. Pat. No. 5,880,188, the content of which is hereby incorporated by reference in its entirety.

In another aspect, provided is a method of using a volatile antimicrobial compound against pathogens affecting meats, plants, or plant parts. The method comprises contacting the meats, plants, or plant parts with an effective amount of the volatile antimicrobial compound of formula (VI):

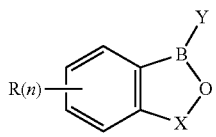
(VI)

wherein each R is independently hydrogen, alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, halogen, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

n=1, 2, 3, or 4;
B is boron;
X=$(CR_2)_m$ where m=1, 2, 3, or 4;
Y is alkyl, alkene, alkyne, haloalkyl, haloalkene, haloalkyne, alkoxy, alkeneoxy, haloalkoxy, aryl, heteroaryl, arylalkyl, arylalkene, arylalkyne, heteroarylalkyl, heteroarylalkene, heteroarylalkyne, hydroxyl, nitrile, amine, ester, carboxylic acid, ketone, alcohol, sulfide, sulfoxide, sulfone, sulfoximine, sulfilimine, sulfonamide, sulfate, sulfonate, nitroalkyl, amide, oxime, imine, hydroxylamine, hydrazine, hydrazone, carbamate, thiocarbamate, urea, thiourea, carbonate, aryloxy, or heteroaryloxy;

with a proviso that R is not aryloxy or heteroaryloxy when Y is hydroxyl;

and agriculturally acceptable salts thereof.

In one embodiment, the volatile antimicrobial compound has a structure of formula (VII):

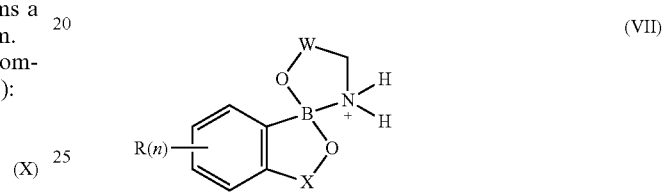
(VII)

wherein W=$(CH_2)_q$ where q is 1, 2, or 3.

In another embodiment, the volatile antimicrobial compound has a structure of

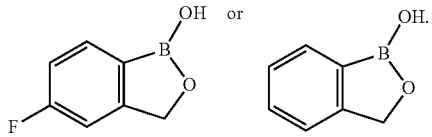 [SMILES: OB1OCc2cc(F)ccc21 ; OB1OCc2ccccc21]

In one embodiment of the method provided, the pathogen is selected from the group consisting of *Alternaria* spp., *Aspergillus* spp., *Botryospheria* spp., *Botrytis* spp., *Byssochlamys* spp., *Colletotrichum* spp., *Diplodia* spp., *Fusarium* spp., *Geotrichum* spp., *Lasiodiplodia* spp., *Monolinia* spp., *Mucor* spp., *Penicillium* spp., *Pezicula* spp., *Phomopsis* spp., *Phytophthora* spp., *Pythium* spp., *Rhizoctonia* spp., *Rhizopus* spp., *Sclerotinia* spp., and *Venturia* spp. In another embodiment, the pathogen is selected from the group consisting of *Erwinia* spp., *Pectobacterium* spp., *Pseudomonas* spp., *Ralstonia* spp., *Xanthomonas* spp.; *Salmonella* spp., *Escherichia* spp., *Listeria* spp., *Bacillus* spp., *Shigella* spp., and *Staphylococcus* spp. In another embodiment, the pathogen is selected from the group consisting of *Candida* spp., *Debaryomyces* spp., *Bacillus* spp., *Campylobacter* spp., *Clostridium* spp., *Cryptosporidium* spp., *Giardia* spp., *Vibrio* spp., and *Yersinia* spp. In another embodiment, the method comprises a pre-harvest treatment or post-harvest treatment. In a further embodiment, the pre-harvest treatment is selected from the group consisting of seed treatment and transplant treatment. In another embodiment, the post-harvest treatment is selected from the group consisting of treatment during field packing, treatment during palletization, in-box treatment, treatment during transportation, and treatment during storage and/or throughout the distribution network.

In another embodiment, the plants or plant parts comprise transgenic plants or transgenic plant parts. In another embodiment, the plants or plant parts are selected from the group consisting of corn, wheat, cotton, rice, soybean, and canola. In another embodiment, the plants or plant parts are selected from the group consisting of fruit, vegetables, nursery, turf and ornamental crops. In a further embodiment, the fruit is selected from the group consisting of banana, pineapple, citrus including oranges, lemon, lime, grapefruit, and other citrus, grapes, watermelon, cantaloupe, muskmelon, and other melons, apple, peach, pear, cherry, kiwifruit, mango, nectarine, guava, papaya, persimmon, pomegranate, avocado, fig, and berries including strawberry, blueberry, raspberry, blackberry, currants and other types of berries. In a further embodiment, the vegetable is selected from the group consisting of tomato, potato, sweet potato, cassava, pepper, bell pepper, carrot, celery, squash, eggplant, cabbage, cauliflower, broccoli, asparagus, mushroom, onion, garlic, leek, and snap bean. A further embodiment, the flower or flower part is selected from the group consisting of roses, carnations, orchids, geraniums, lily or other ornamental flowers. A further embodiment, the meat is selected from the group of beef, bison, chicken, deer, goat, turkey, pork, sheep, fish, shellfish, mollusks, or dry-cured meat products.

In one embodiment, the contacting comprises applying the volatile antimicrobial compound by ways selected from the group consisting of spray, mist, thermal or non-thermal fogging, drench, gas treatment, and combinations thereof. In a further embodiment, the gas treatment is selected from the group consisting of release from a sachet, release from a synthetic or natural film, fibrous material, and/or release from a liner or other packaging materials, release from powder, release from a gas-releasing generator, release using a compressed or non-compressed gas cylinder, release from a droplet inside a box, and combinations thereof. In another embodiment, the method further comprises contacting the meats, plants, plant parts with a cyclopropene compound. In a further embodiment, the cyclopropene compound comprises 1-methylcyclopropene (1-MCP).

In another aspect, provided is a method of using a volatile antimicrobial compound against pathogens affecting meats, plants, or plant parts. The method comprises contacting the meats, plants, or plant parts with an effective amount of the volatile antimicrobial compound of formula (VIII):

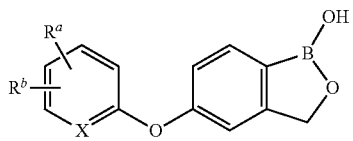

(VIII)

wherein $R^a$ is CN, C(O)NR$^9$R$^{10}$, or C(O)OR$^{11}$ wherein R$^{11}$ is hydrogen, substituted alkyl, or unsubstituted alkyl,
X is N, CH and CR$^b$;
$R^b$ is halogen, substituted or unsubstituted alkyl, C(O)R$^{12}$, C(O)OR$^{12}$, OR$^{12}$, NR$^{12}$R$^{13}$, wherein R$^9$, R$^{10}$, R$^{12}$, and R$^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
with a proviso that R$^9$ and R$^{10}$, together with the atoms to which they are attached, are optionally combined to form a 4- to 8-membered substituted or unsubstituted heterocycloalkyl ring;
and with a proviso that R$^{12}$ and R$^{13}$, together with the atoms to which they are attached, are optionally combined to form a 4- to 8-membered substituted or unsubstituted heterocycloalkyl ring;
and agriculturally acceptable salts thereof.

In one embodiment, the volatile antimicrobial compound of the invention has the structure of formula (XI):

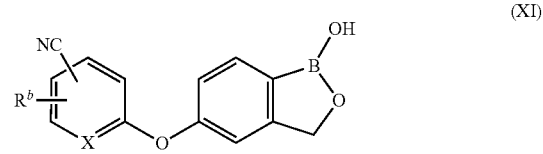

(XI)

In another embodiment, the volatile antimicrobial compound of the invention is selected from:

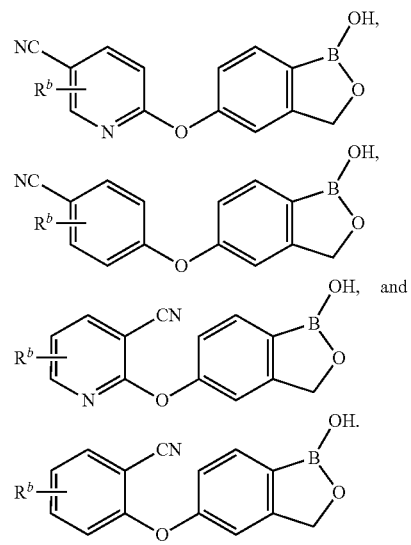

In another embodiment, the volatile antimicrobial compound of the invention is selected from:

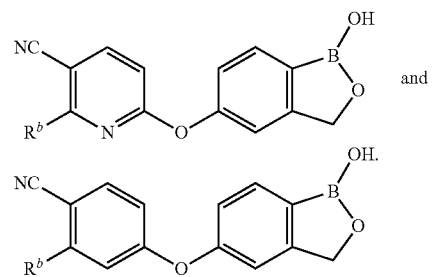

In another embodiment, the volatile antimicrobial compound of the invention is selected from:

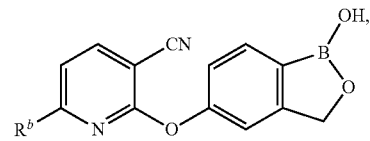

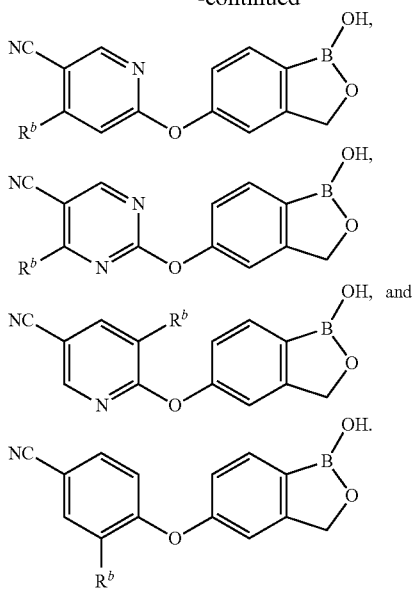

In one embodiment, the volatile antimicrobial compound of the invention has the structure of formula (XII):

(XII)

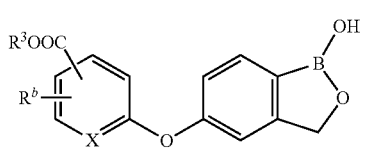

In another embodiment, the volatile antimicrobial compound of the invention is selected from:

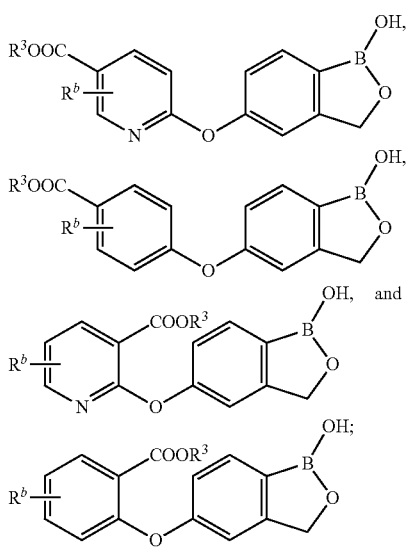

wherein R³ is hydrogen, substituted or unsubstituted alkyl, or substituted or unsubstituted heteroalkyl.

In another embodiment, the volatile antimicrobial compound of the invention is selected from:

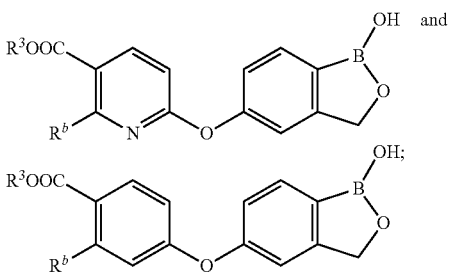

wherein R³ is hydrogen, substituted or unsubstituted alkyl, or substituted or unsubstituted heteroalkyl.

In another embodiment, the volatile antimicrobial compound of the invention is selected from:

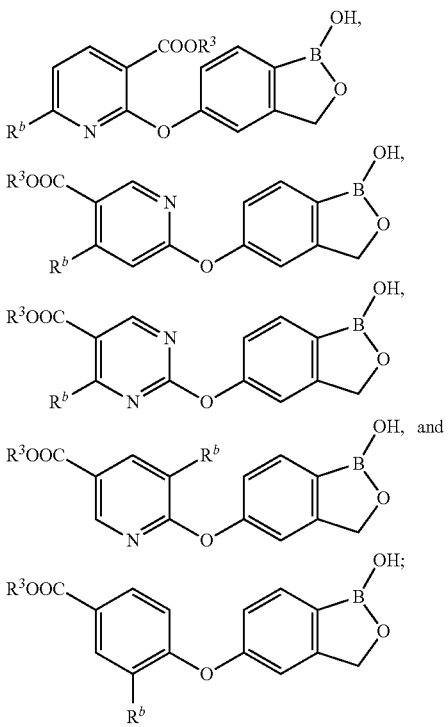

wherein R³ is hydrogen, substituted or unsubstituted alkyl, or substituted or unsubstituted heteroalkyl.

In one embodiment, the volatile antimicrobial compound of the invention has the structure of formula (XIII):

(XIII)

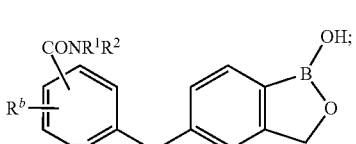

wherein each of R¹ and R² is independently hydrogen, substituted or unsubstituted alkyl, or substituted or unsubstituted heteroalkyl.

In another embodiment, the volatile antimicrobial compound of the invention is selected from:

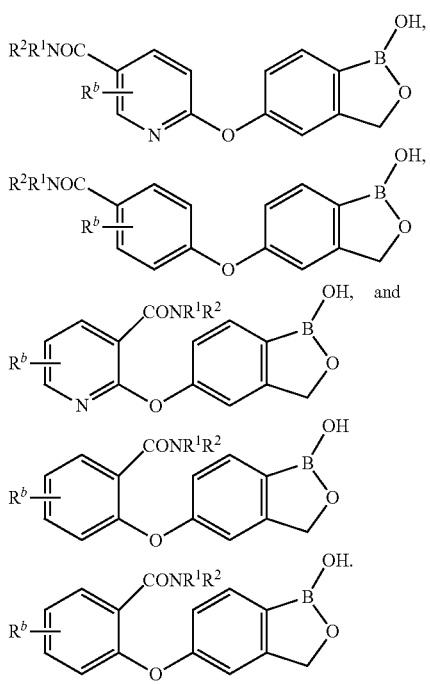

In another embodiment, the volatile antimicrobial compound of the invention is selected from:

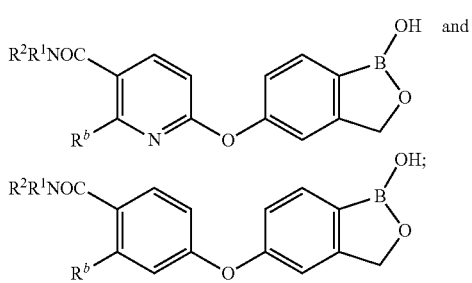

wherein each of $R^1$ and $R^2$ is independently hydrogen, substituted or unsubstituted alkyl, or substituted or unsubstituted heteroalkyl.

In another embodiment, the volatile antimicrobial compound of the invention is selected from:

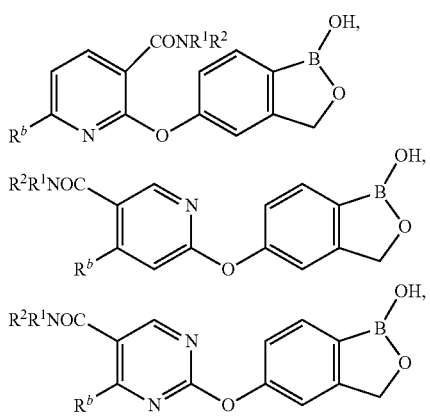

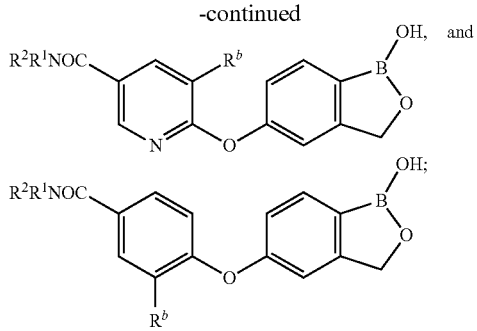

wherein each of $R^1$ and $R^2$ is independently hydrogen, substituted or unsubstituted alkyl, or substituted or unsubstituted heteroalkyl.

In one embodiment, $R^b$ is selected from fluorine and chlorine. In another embodiment, $R^b$ is selected from $OR^{26}$ and $NR^{27}R^{28}$. In another embodiment when $R^b$ is $OR^{26}$, $R^{26}$ is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $OR^{26}$, $R^{26}$ is selected from H, substituted or unsubstituted alkyl, substituted or unsubstituted heteroalkyl and substituted or unsubstituted cycloalkyl. In another embodiment when $R^b$ is $OR^{26}$, $R^{26}$ is unsubstituted $C_1$-$C_6$ alkyl. In another embodiment when $R^b$ is $OR^{26}$, $R^{26}$ is unsubstituted cycloalkyl. In another embodiment when $R^b$ is $OR^{26}$, $R^{26}$ is alkyl, substituted with a member selected from substituted or unsubstituted $C_1$-$C_6$ alkoxy. In another embodiment when $R^b$ is $OR^{26}$, $R^{26}$ is alkyl, substituted with at least one halogen. In another embodiment when $R^b$ is $OR^{26}$, $R^{26}$ is alkyl, substituted with at least one oxo moiety.

In another embodiment when $R^b$ is $OR^{26}$, $R^{26}$ is a member selected from —$CH_3$, —$CH_2CH_3$, —$(CH_2)_2CH_3$, —$CH(CH_3)_2$, —$CH_2CF_3$, —$CH_2CHF_2$, —$CH_2CH_2(OH)$, —$CH_2CH_2(OCH_3)$, —$CH_2CH_2(OC(CH_3)_2)$, —$C(O)CH_3$, —$CH_2CH_2OC(O)CH_3$, —$CH_2C(O)OCH_2CH_3$, —$CH_2C(O)OC(CH_3)_3$, —$(CH_2)_3C(O)CH_3$, —$CH_2C(O)OC(CH_3)_3$, cyclopentyl, cyclohexyl,

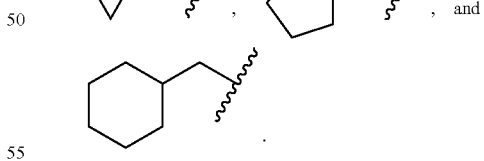

In another embodiment when $R^b$ is $NR^{27}R^{28}$, $R^{27}$ and $R^{28}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In another embodiment when $R^b$ is $NR^{27}R^{28}$, $R^{27}$ is H or unsubstituted alkyl; and $R^{28}$ is unsubstituted alkyl or alkyl substituted with a member selected from hydroxyl, phenyl, unsubstituted alkoxy and alkoxy substituted with a phenyl. In a further embodiment when $R^b$ is $NR^{27}R^{28}$, $R^{27}$ is H or $CH_3$.

In another embodiment when $R^b$ is $NR^{27}R^{28}$, $R^{27}$ and $R^{28}$ are independently selected from substituted or unsubstituted alkyl. In another embodiment when $R^b$ is $NR^{27}R^{28}$, $R^{27}$ is unsubstituted alkyl; and $R^{28}$ is substituted or unsubstituted alkyl. In another embodiment when $R^b$ is $NR^{27}R^{28}$, $R^{27}$ is unsubstituted alkyl; and $R^{28}$ is alkyl, substituted with a member selected from substituted or unsubstituted alkoxy and hydroxyl. In another embodiment when $R^b$ is $NR^{27}R^{28}$, $R^{27}$ is unsubstituted alkyl; and $R^{28}$ is alkyl, substituted with unsubstituted alkoxy. In another embodiment when $R^b$ is $NR^{27}R^{28}$, $R^{27}$ is unsubstituted alkyl; and $R^{28}$ is alkyl, substituted with alkoxy, substituted with phenyl. In another embodiment when $R^b$ is $NR^{27}R^{28}$, $R^{27}$ is unsubstituted alkyl; and $R^{28}$ is alkyl, substituted with unsubstituted alkoxy. In another embodiment when $R^b$ is $NR^{27}R^{28}$, $R^{27}$ and $R^{28}$ together with the nitrogen to which they are attached, are combined to form a 4- to 8-membered substituted or unsubstituted heterocycloalkyl ring. In another embodiment when $R^b$ is $NR^{27}R^{28}$, $R^{27}$ and $R^{28}$ together with the nitrogen to which they are attached, are combined to form a 5- or 6-membered substituted or unsubstituted heterocycloalkyl ring.

In another embodiment, $R^b$ is selected from $N(CH_3)_2$, $N(CH_3)(CH_2CH_2(OCH_3))$, $N(CH_3)(CH_2CH_2OH)$, $NH_2$, $NHCH_3$, $NH(CH_2CH_2(OCH_3))$, $NH(CH_2CH_2(OCH_2Ph)$, $NH(CH_2Ph)$, $NH(C(CH_3)_3)$ and $NH(CH_2CH_2OH)$. In another embodiment, Rb is selected from

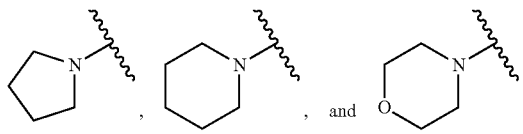

Additional antimicrobial compounds are also disclosed previously in U.S. Pat. No. 8,039,450, and patent application publication US 2009/0291917, the contents of which are hereby incorporated by reference in their entireties.

The practice of the present invention involves the use of one or more cyclopropene compound. As used herein, a cyclopropene compound is any compound with the formula

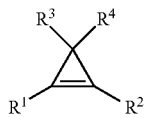

where each $R^1$, $R^2$, $R^3$ and $R^4$ is independently selected from the group consisting of H and a chemical group of the formula:

where n is an integer from 0 to 12. Each L is a bivalent radical. Suitable L groups include, for example, radicals containing one or more atoms selected from H, B, C, N, O, P, S, Si, or mixtures thereof. The atoms within an L group may be connected to each other by single bonds, double bonds, triple bonds, or mixtures thereof. Each L group may be linear, branched, cyclic, or a combination thereof. In any one R group (i.e., any one of $R^1$, $R^2$, $R^3$ and $R^4$) the total number of heteroatoms (i.e., atoms that are neither H nor C) is from 0 to 6. Independently, in any one R group the total number of non-hydrogen atoms is 50 or less. Each Z is a monovalent radical. Each Z is independently selected from the group consisting of hydrogen, halo, cyano, nitro, nitroso, azido, chlorate, bromate, iodate, isocyanato, isocyanido, isothiocyanato, pentafluorothio, and a chemical group G, wherein G is a 3- to 14-membered ring system.

The $R^1$, $R^2$, $R^3$, and $R^4$ groups are independently selected from the suitable groups. Among the groups that are suitable for use as one or more of $R^1$, $R^2$, $R^3$, and $R^4$ are, for example, aliphatic groups, aliphatic-oxy groups, alkylphosphonato groups, cycloaliphatic groups, cycloalkylsulfonyl groups, cycloalkylamino groups, heterocyclic groups, aryl groups, heteroaryl groups, halogens, silyl groups, other groups, and mixtures and combinations thereof. Groups that are suitable for use as one or more of $R^1$, $R^2$, $R^3$, and $R^4$ may be substituted or unsubstituted.

Among the suitable $R^1$, $R^2$, $R^3$, and $R^4$ groups are, for example, aliphatic groups. Some suitable aliphatic groups include, for example, alkyl, alkenyl, and alkynyl groups. Suitable aliphatic groups may be linear, branched, cyclic, or a combination thereof. Independently, suitable aliphatic groups may be substituted or unsubstituted.

As used herein, a chemical group of interest is said to be "substituted" if one or more hydrogen atoms of the chemical group of interest is replaced by a substituent.

Also among the suitable $R^1$, $R^2$, $R^3$, and $R^4$ groups are, for example, substituted and unsubstituted heterocyclyl groups that are connected to the cyclopropene compound through an intervening oxy group, amino group, carbonyl group, or sulfonyl group; examples of such $R^1$, $R^2$, $R^3$, and $R^4$ groups are heterocyclyloxy, heterocyclylcarbonyl, diheterocyclylamino, and diheterocyclylaminosulfonyl.

Also among the suitable $R^1$, $R^2$, $R^3$, and $R^4$ groups are, for example, substituted and unsubstituted heterocyclic groups that are connected to the cyclopropene compound through an intervening oxy group, amino group, carbonyl group, sulfonyl group, thioalkyl group, or aminosulfonyl group; examples of such $R^1$, $R^2$, $R^3$, and $R^4$ groups are diheteroarylamino, heteroarylthioalkyl, and diheteroarylaminosulfonyl.

Also among the suitable $R^1$, $R^2$, $R^3$, and $R^4$ groups are, for example, hydrogen, fluoro, chloro, bromo, iodo, cyano, nitro, nitroso, azido, chlorato, bromato, iodato, isocyanato, isocyanido, isothiocyanato, pentafluorothio, acetoxy, carboethoxy, cyanato, nitrato, nitrito, perchlorato, allenyl, butylmercapto, diethylphosphonato, dimethylphenylsilyl, isoquinolyl, mercapto, naphthyl, phenoxy, phenyl, piperidino, pyridyl, quinolyl, triethylsilyl, trimethylsilyl, and substituted analogs thereof.

As used herein, the chemical group G is a 3- to 14-membered ring system. Ring systems suitable as chemical group G may be substituted or unsubstituted; they may be aromatic (including, for example, phenyl and napthyl) or aliphatic (including unsaturated aliphatic, partially saturated aliphatic, or saturated aliphatic); and they may be carbocyclic or heterocyclic. Among heterocyclic G groups, some suitable heteroatoms are, for example, nitrogen, sulfur, oxygen, and combinations thereof. Ring systems suitable as chemical group G may be monocyclic, bicyclic, tricyclic, polycyclic, spiro, or fused; among suitable chemical group G ring systems that are bicyclic, tricyclic, or fused, the various rings in a single chemical group G may be all the same type or may be of two or more types (for example, an aromatic ring may be fused with an aliphatic ring).

In one embodiment, one or more of $R^1$, $R^2$, $R^3$, and $R^4$ is hydrogen or $(C_1-C_{10})$ alkyl. In another embodiment, each of $R^1$, $R^2$, $R^3$, and $R^4$ is hydrogen or $(C_1-C_8)$ alkyl. In another embodiment, each of $R^1$, $R^2$, $R^3$, and $R^4$ is hydrogen or $(C_1-C_4)$ alkyl. In another embodiment, each of $R^1$, $R^2$, $R^3$, and $R^4$ is hydrogen or methyl. In another embodiment, $R^1$ is ($C_1$-$C_4$) alkyl and each of $R^2$, $R^3$, and $R^4$ is hydrogen. In another embodiment, $R^1$ is methyl and each of $R^2$, $R^3$, and $R^4$ is hydrogen, and the cyclopropene compound is known herein as 1-methylcyclopropene or "1-MCP."

In another embodiment, the cyclopropene is of the formula:

wherein R is a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy. In one embodiment, R is $C_1$-$C_8$ alkyl. In another embodiment, R is methyl.

In another embodiment, the cyclopropene is of the formula:

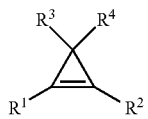

wherein $R^1$ is a substituted or unsubstituted $C_1$-$C_4$ alkyl, $C_1$-$C_4$ alkenyl, $C_1$-$C_4$ alkynyl, $C_1$-$C_4$ cycloalkyl, cycloalkylalkyl, phenyl, or napthyl group; and $R^2$, $R^3$, and $R^4$ are hydrogen. In another embodiment, the cyclopropene comprises 1-methylcyclopropene (1-MCP).

As used herein, the phrase "transgene vector" refers to a vector that contains an inserted segment of deoxyribonucleic acid (DNA), the "transgene" that is transcribed into messenger ribonucleic acid (mRNA) or replicated as ribonucleic acid (RNA) within a host cell. The phrase "transgene" refers not only to that portion of inserted DNA that is converted into RNA, but also those portions of the vector that are necessary for the transcription or replication of the RNA. A transgene typically comprises a gene-of-interest but needs not necessarily comprise a polynucleotide sequence that contains an open reading frame capable of producing a protein.

Meats, plants, or plant parts may be treated in the practice of the present invention. One example is treatment of whole plants; another example is treatment of whole plants while they are planted in soil, prior to the harvesting of useful plant parts.

Any plants that provide useful plant parts may be treated in the practice of the present invention. Examples include plants that provide fruits, vegetables, and grains.

As used herein, the phrase "plant" includes dicotyledonous plants and monocotyledonous plants. Examples of dicotyledonous plants include tobacco, Arabidopsis, soybean, tomato, papaya, canola, sunflower, cotton, alfalfa, potato, grapevine, pigeon pea, pea, Brassica, chickpea, sugar beet, rapeseed, watermelon, melon, pepper, peanut, pumpkin, radish, spinach, squash, broccoli, cabbage, carrot, cauliflower, celery, Chinese cabbage, cucumber, eggplant, and lettuce. Examples of monocotyledonous plants include corn, rice, wheat, sugarcane, barley, rye, sorghum, orchids, bamboo, banana, cattails, lilies, oat, onion, millet, and triticale. Examples of fruit include banana, pineapple, oranges, grapes, grapefruit, watermelon, melon, apples, peaches, pears, kiwifruit, mango, nectarines, guava, persimmon, avocado, lemon, fig, and berries.

Those skilled in the art would understand certain variation can exist based on the disclosure provided. Thus, the following examples are given for the purpose of illustrating the invention and shall not be construed as being a limitation on the scope of the invention or claims.

EXAMPLES

Example 1

12-Well (7 milliliter (mL volume per well) microtiter plates are used for the in vitro inhibition assay for volatile antimicrobial compounds. A 3-mL volume of full-strength Potato Dextrose Agar (PDA) is added to each well. After cooling, 1 microliter (μL) of $1\times10^6$ per mL Botrytis cinerea spore suspension is spot pipetted to the center of the agar. For the first experiment, inoculated plates are allowed to germinate for 5 days at 4° C. For the second experiment, plates are inoculated immediately prior to volatile fungicide treatment. Small Whatman #1 filter disks (Cat. No. 1001-0155) are placed, in duplicate, on the underside of a polyethylene PCR plate sealing film.

TABLE 1

Results of in vitro assay for volatile fungicide

| Rate of Compound A (mg per disk) | Botrytis inhibition % (in vitro) |
|---|---|
| 1.25 | 100% |
| 0.63 | 100% |
| 0.31 | 100% |
| 0.16 | 100% |
| 0.08 | 100% |
| 0.04 | 100% |
| 0.023 | 100% |
| 0.01 | 100% |
| 0.005 | 100% |
| 0.0024 | 85% |
| 0.001 | 69% |
| 0.0006 | 46% |
| Control | 0% |

For determination of the minimum inhibitory concentration (MIC), Compound A (benzoxaborole; FIG. 1) is diluted in acetone, and the appropriate amount of compound is added to disks in a dose dependent manner (1.25 to 0.0006 milligrams per disk (mg/disk)). The acetone is permitted to evaporate for 5 minutes. The headspace around the Botrytis cinerea inoculum is then sealed inside the well by the film with the adhering disk containing the fungicide. Plates are inverted, placed over the treated disks and sealed to prevent any of the chemical from flaking from the disk and falling onto the inoculated agar. After 14 days of storage at 4° C., cultures are evaluated for percent growth relative to control. Regardless of whether the spores had germinated for 5 days, or if the treatment commenced soon after inoculation of the plates (~15 minutes); there is 100% control of the fungal pathogen down to 0.005 mg. Experimental results are summarized in Table 1. The results suggest that Compound A is able to kill Botrytis cinerea spores and inhibit mycelial growth at the same concentration. Thus, Compound A (FIG. 1) shows 100% efficacy in the in vitro inhibition of fungal growth at a rate of 0.005 mg/disk.

Example 2

Figure 3:
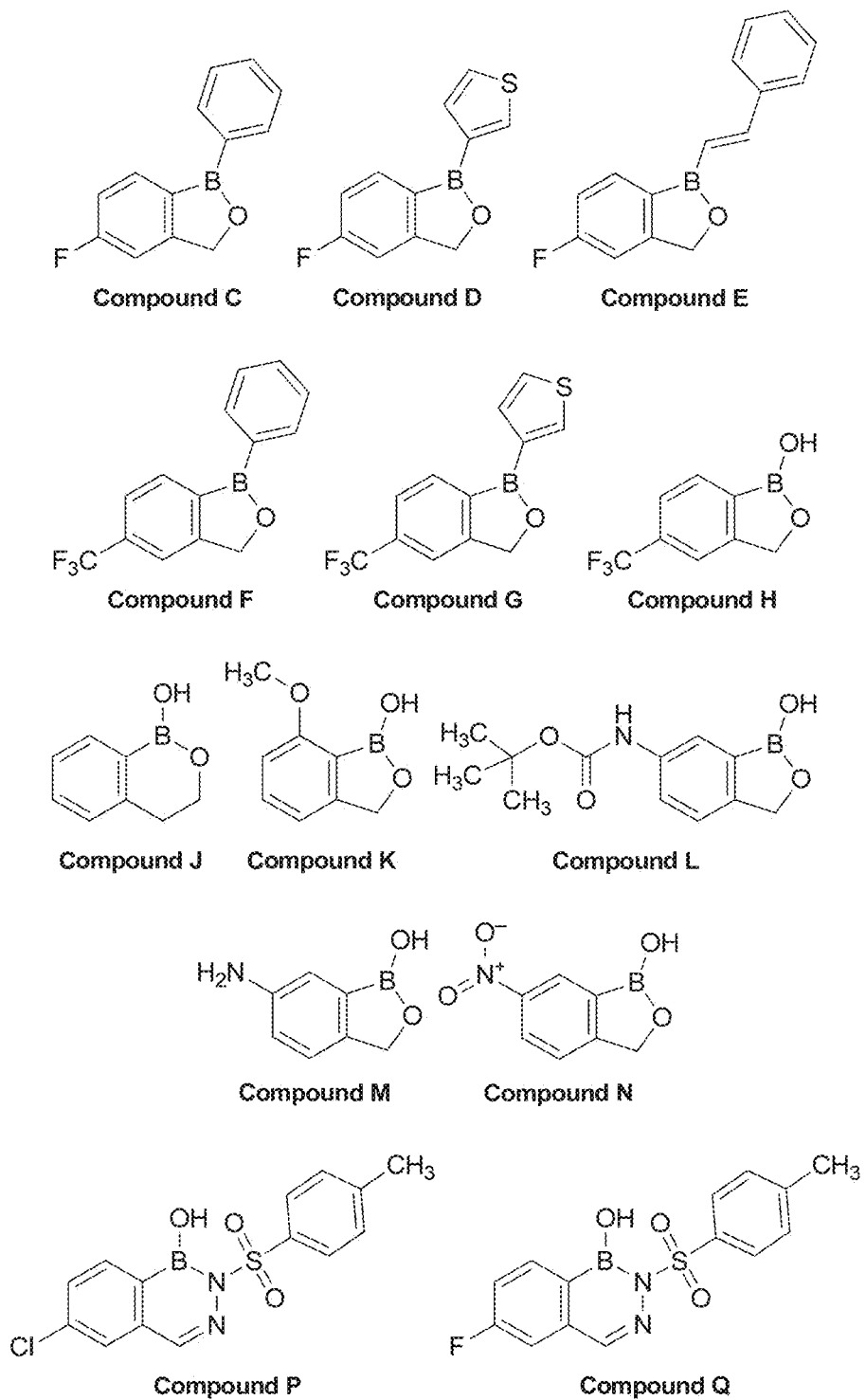
FIG. 3 shows fourteen compounds tested in Example 2.
Figure 4A:
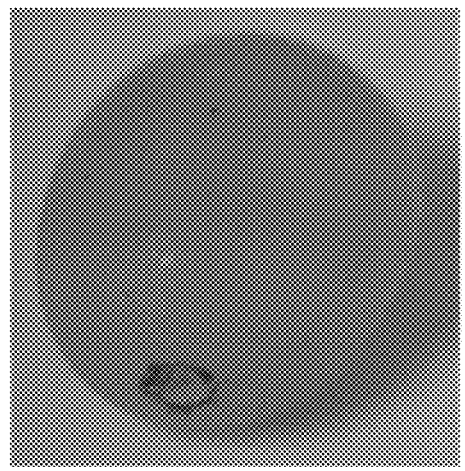
FIGS. 4A-4D show representative photos of exemplary in vivo inhibition results in a green table grape inoculated with *Botrytis cinerea* and treated using Compound A as described in Example 4, where 0.04 mg of Compound A shows 100% inhibition and 0.0024 mg of Compound A shows no inhibition.
Figure 4B:
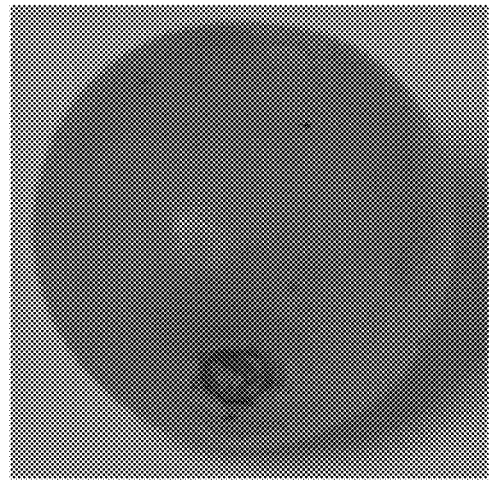
Figure 4C:
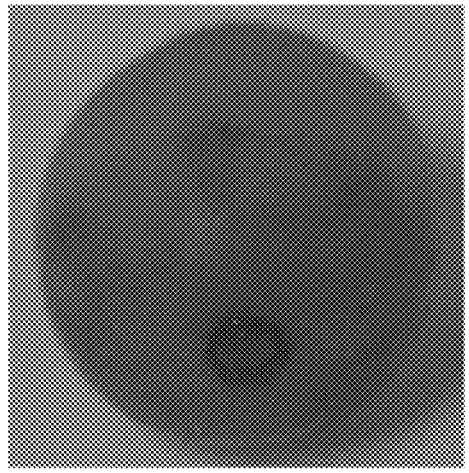
Figure 4D:
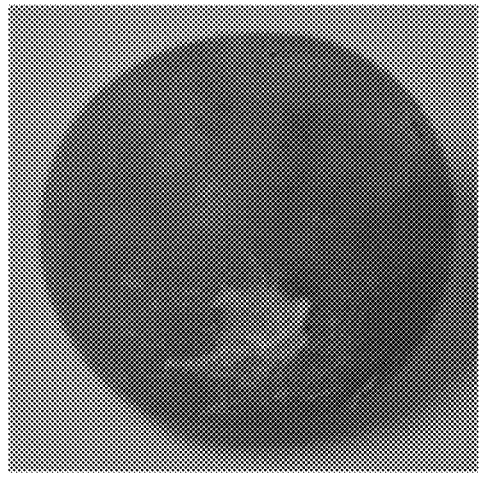

A total of 14 antimicrobial compounds are tested using the in vitro inhibition assay described in Example 1. All 14 compounds are applied to the Whatman disks, in duplicate, in a dose dependent manner (0.31 to 0.0006 mg/disk). The results show that Compound A provides the best control of *Botrytis cinerea*, with 100% control down to 0.005 mg/disk. Other compounds, such as Compound C, Compound D, and Compound E conferred 100% control down to 0.023, 0.04, and 0.08 mg/disk, respectively. The tested compounds are shown in FIG. 3. Results of nine compounds are summarized in Table 2, where the other five compounds show no detected activity in the ranges tested.

TABLE 2

Results of in vitro assay for volatile fungicide in % *Botrytis* inhibition

| Rate (mg/disk) | Comp. A | Comp. C | Comp. D | Comp. E | Comp. F | Comp. G | Comp. H | Comp. J | Comp. K |
|---|---|---|---|---|---|---|---|---|---|
| 0.31 | 100% | 100% | 100% | 100% | 70% | 100% | 85% | 50% | 48% |
| 0.16 | 100% | 100% | 100% | 100% | 53% | 78% | 80% | 13% | 29% |
| 0.08 | 100% | 100% | 100% | 100% | 40% | 43% | 55% | 8% | 5% |
| 0.04 | 100% | 100% | 100% | 79% | 18% | 13% | 38% | 5% | 0% |
| 0.023 | 100% | 100% | 80% | 79% | 10% | 3% | 18% | 0% | 0% |
| 0.01 | 100% | 83% | 70% | 69% | 8% | 0% | 3% | 0% | 0% |
| 0.005 | 100% | 63% | 38% | 38% | 8% | 0% | 0% | 0% | 0% |
| 0.0024 | 85% | 43% | 15% | 28% | 0% | 0% | 0% | 0% | 0% |
| 0.001 | 69% | 15% | 0% | 13% | 0% | 0% | 0% | 0% | 0% |
| 0.0006 | 46% | 0% | 0% | 13% | 0% | 0% | 0% | 0% | 0% |
| Control | 0% | 0% | 0% | 0% | 0% | 0% | 0% | 0% | 0% |

Example 3

Figure 2:
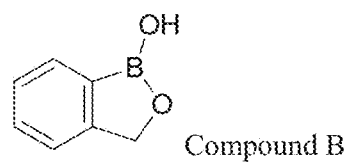
FIG. 2 shows the chemical structure of an exemplary Compound B of the invention.

Compound B (FIG. 2; 2-(hydroxymethyl)phenylboronic acid cyclic monoester, a des-fluoro analogue of Compound A), is evaluated in a similar manner as described in Examples 1 and 2 above. The compound is applied to the Whatman filter paper at rates from 0.5 mg to 0.0039 mg/disk. Results show that Compound B inhibits 100% *Botrytis cinerea* at a rate of 0.0078 mg/disk.

Example 4

In order to assess the in vivo activity of volatile antimicrobial compounds, a volatile bioassay is developed using green table grape. Fruit are placed individually inside a 20 mL scintillation vial, with the stem wound facing upwards. The fresh stem wound is inoculated with 10 μL of 1×10⁶ per mL *Botrytis cinerea* spore suspension. Whatman filter paper (Cat. No. 1822-024) is placed inside duplicate vial caps. For determination of the MIC, Compound A (FIG. 1) is diluted in acetone, and the appropriate amount of compound is added to the disks in a dose dependent manner (2.5 to 0.0024 mg/disk). The acetone is permitted to evaporate for 5 minutes. The vials are then capped with the lids containing the fungicide, and placed for 14 days at 4° C. After storage, fruit are evaluated for incidence of disease and appearance of phytotoxicity. Results are summarized in Table 3 and there is 100% control of *Botrytis cinerea* down to 0.04 mg/disk and no evidence of phytotoxicity at any of the rates evaluated. Representative photos of exemplary in vivo inhibition results using Compound A are shown in FIGS. 4A-4D, where 0.04 mg of Compound A shows 100% inhibition and 0.0024 mg of Compound A shows no inhibition.

TABLE 3

Results of in vivo assay for volatile fungicide

| Rate of Compound A (mg per disk) | *Botrytis* inhibition % (in vivo) |
|---|---|
| 1.25 | 100% |
| 0.63 | 100% |
| 0.31 | 100% |

TABLE 3-continued

Results of in vivo assay for volatile fungicide

| Rate of Compound A (mg per disk) | *Botrytis* inhibition % (in vivo) |
|---|---|
| 0.16 | 100% |
| 0.08 | 100% |
| 0.04 | 100% |
| 0.023 | 0% |
| 0.01 | 0% |
| 0.005 | 0% |
| 0.0024 | 0% |
| Control | 0% |

Example 5

In order to assess the in vivo activity of volatile antimicrobial compounds, a volatile bioassay is developed using strawberry. Two fruit are placed inside a 240 mL jar, with the calyx facing downwards. A fresh wound is inoculated with 20 μL of 1×10⁶ per mL *Botrytis cinerea* spore suspension. Whatman filter paper (Cat. No. 1822-024) is placed inside duplicate jar lids. For determination of the MIC, Compound A (benzoxaborole; FIG. 1) is diluted in acetone, and the appropriate amount of compound is added to the disks in a dose dependent manner (2.5 to 0.005 mg/disk). For determination of the MIC, Compound B (benzoxaborole; FIG. 2) is diluted in acetone, and the appropriate amount of compound is added to the disks in a dose dependent manner (2.5 to 0.005 mg/disk). The acetone is permitted to evaporate for 5 minutes. The jars are then capped with the lids containing the fungicide, and placed for 5 days at 21° C. After storage, fruit are evaluated for incidence and severity of disease and appearance of phytotoxicity. Results are summarized in Table 4. There is 100% control of *Botrytis cinerea* down to 0.16 mg/disk for Compound A and 100% control of *Botrytis cinerea* down to 0.32 mg/disk for Compound B, and no evidence of phytotoxicity at any of the rates evaluated.

TABLE 4

Percent (%) Incidence of *Botrytis cinerea* on Strawberry (in vivo)

| Rates (mg/disk) | Compound A | Compound B |
|---|---|---|
| 0.005 | 75% | 100% |
| 0.01 | 100% | 100% |
| 0.02 | 50% | 100% |
| 0.04 | 75% | 75% |
| 0.08 | 0% | 50% |
| 0.16 | 0% | 25% |
| 0.32 | 0% | 0% |
| 0.64 | 0% | 0% |
| 1.25 | 0% | 0% |
| 2.5 | 0% | 0% |

Example 6

Figure 5A:
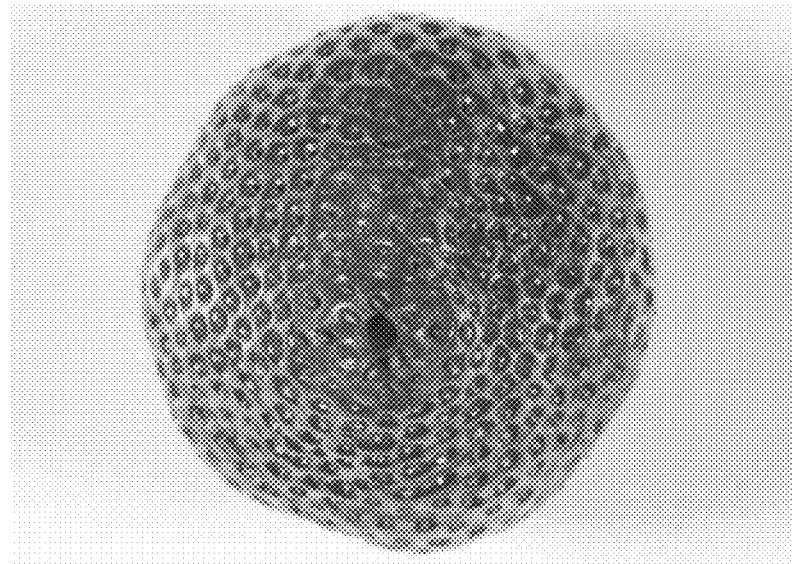
FIGS. 5A and 5B show representative photos of exemplary in vivo inhibition results in a strawberry inoculated with *Botrytis cinerea* and treated using Compound A as described in Example 6, where 0.125 mg of Compound A shows 100% inhibition.
Figure 5B:
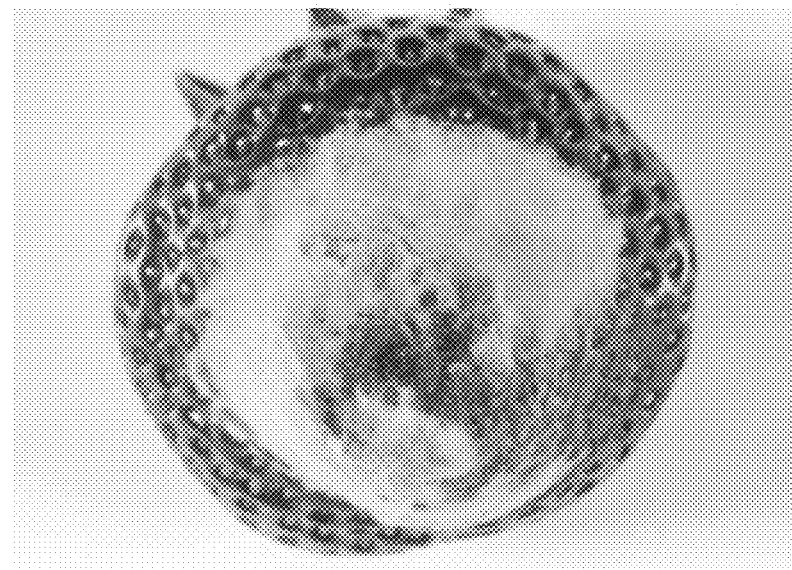

In order to assess the in vivo dose by time activity of volatile antimicrobial compounds, a volatile bioassay is developed using strawberry. Two fruit are placed inside a 240 mL jar, with the calyx facing downwards. A fresh wound is inoculated with 20 μL of 1×10$^6$ per ml *Botrytis cinerea* spore suspension. Whatman filter paper (Cat. No. 1822-024) is placed inside duplicate jar lids. Compound A (benzoxaborole; FIG. 1) is diluted in acetone, and the appropriate amount of compound is added to the disks at two rates 0.008 or 0.125 mg. The acetone is permitted to evaporate for 5 minutes. The jars are capped with the lids containing the fungicide, and incubated with the volatile fungicide for 1, 3, 6, 24 or 72 hours. After incubation, lids containing the disk with Compound A are replaced with new lids without Compound A. All samples are maintained at 21° C. for 3 days, and then the lids are removed and maintained for an additional 48 hours, all at 90% relative humidity (R.H.). The fruit are evaluated for incidence and severity of disease and appearance of phytotoxicity. Results are summarized in Table 5. There is 100% control of *Botrytis cinerea* at 0.125 mg/disk for Compound A after 6 hour exposure, and no evidence of phytotoxicity. 0.125 mg of Compound A shows 100% in vivo inhibition in comparison to the acetone only control. A representative result is also shown in FIGS. 5A and 5B.

TABLE 5

Incidence (%) and Severity of *Botrytis cinerea* on strawberries over time

| | Compound A | | | |
|---|---|---|---|---|
| | Incidence (%) | | Severity (0 to 3) | |
| | Rates (mg/disk) | | | |
| Time (h) | 0.008 | 0.125 | 0.008 | 0.125 |
| 1 | 100% | 67% | 4.0 | 2.3 |
| 3 | 0% | 33% | 0.0 | 1.3 |
| 6 | 33% | 0% | 1.0 | 0.0 |
| 24 | 67% | 0% | 2.3 | 0.0 |
| 72 | 33% | 0% | 1.0 | 0.0 |

Severity:
0 = no fungal growth
1 = slight infection (<5 millimeter (mm) diameter)
2 = moderate infection (<1 centimeter (cm) diameter)
3 = high infection (>1 cm diameter)
4 = extreme infection (> half-length of fruit)

Example 7

12-Well (7 mL volume per well) microtiter plates are used for the in vitro inhibition assay for volatile antimicrobial compounds. A 3-mL volume of full-strength LB Agar is added to each well. After cooling, 15 μL of *Escherichia coli*, adjusted to an optical density of 0.02 to 0.035, and further diluted 1/10 is pipetted to the center of the agar and tilted to distribute uniformly. Small Whatman #1 filter disks (Cat. No. 1001-0155) are placed, in duplicate, on the underside of a polyethylene polymerase chain reaction (PCR) plate sealing film. For determination of the minimum inhibitory concentration (MIC), Compound A (benzoxaborole; FIG. 1) is diluted in acetone, and 5 mg of compound is added to the disks. The acetone is permitted to evaporate for 5 minutes. The headspace around the *Escherichia coli* inoculum is then sealed inside the well by the film with the adhering disk containing the fungicide. Plates are inverted, placed over the treated disks and sealed to prevent any of the chemical from flaking from the disk and falling onto the inoculated agar. After 3 days of storage at 4° C., cultures were transferred to 23° C. for an additional 2 days, and then evaluated for colony growth relative to control. Experimental results are summarized in

TABLE 6

The results suggest that Compound A is able to inhibit *Escherichia coli*.
Table 6. Results of in vitro assay for volatile fungicide

| Rate of Compound A (mg per disk) | Colony Rating |
|---|---|
| 5.00 | 1 |
| Untreated | 3 |
| Not Inoculated | 0 |

Colony Rating:
0 = No colonies
1 = Micro colonies not connected
2 = Small colonies with some merging
3 = Large colonies merging together

Example 8

12-Well (6.5 mL volume per well) microtiter plates are used for the in vitro inhibition assay for volatile antimicrobial compounds. A 3-mL volume of full-strength Potato Dextrose Agar (PDA) is added to each well. After cooling, 1 μL of 1×10$^5$ per mL *Botrytis cinerea, Penicillium expansum, Alternaria alternata, Monilinia fructicola* or *Glomerella cingulata* spore suspension is spot-pipetted to the center of the agar. Plates are inoculated immediately prior to volatile fungicide treatment. A Whatman #1 filter disk (Cat. No. 1001-0155) is placed, in duplicate, on the underside of a polyethylene PCR plate sealing film. For determination of the minimum inhibitory concentration (MIC), compounds are diluted in acetone, and the appropriate amount of compound is added to the disks in a dose dependent manner to achieve a final headspace concentration of 1142.9 to 0.6 mg/L. The acetone is permitted to evaporate for 5 minutes. The headspace around the inoculum is then sealed inside the well by the film with the adhering disk containing the fungicide by inverting the plates over the treated disks and sealing to prevent any of the chemical from flaking from the disk and falling onto the inoculated agar. After 3 days of storage at 23° C., the cultures are evaluated for percent growth relative to control based on measurement of fungal colony diameter. Experimental results are summarized in Table 7. The results indicate that benzoxaborole compounds have excellent in vitro activity against five selected plant fungal pathogens.

TABLE 7

MIC (mg/L, headspace concentration) of numerous benzoxaborole compounds applied as a volatile treatment against numerous plant fungal pathogens (Compound 10 is the same as Compound A, and Compound 11 is the same as Compound B).

| Structure | Cmpd # | MIC (mg/L) | | | | |
|---|---|---|---|---|---|---|
| | | BOTRCI | PENIEX | ALTEAL | MONIFC | GLOMCI |
| (structure) | 6 | 2.2 | 17.9 | 4.5 | 8.9 | 17.9 |
| (structure) | 7 | 2.2 | 17.9 | 8.9 | 8.9 | 71.4 |
| (structure) | 8 | 2.2 | 35.7 | 8.9 | 4.5 | 71.4 |
| (structure) | 9 | 2.2 | 8.9 | 8.9 | 8.9 | 35.7 |
| (structure) | 10 | 2.2 | 2.2 | <0.6 | <0.6 | <0.6 |
| (structure) | 11 | 4.5 | 17.9 | 4.5 | 2.2 | 35.7 |
| (structure) | 30 | 2.2 | 8.9 | 2.2 | 2.2 | n/a |
| (structure) | 34 | <0.6 | 2.2 | 2.2 | n/a | n/a |
| (structure) | 200 | 10.6 | 68.3 | 7.3 | 6.3 | n/a |

TABLE 7-continued

MIC (mg/L, headspace concentration) of numerous benzoxaborole compounds applied as a volatile treatment against numerous plant fungal pathogens (Compound 10 is the same as Compound A, and Compound 11 is the same as Compound B).

| Structure | Cmpd # | BOTRCI | PENIEX | ALTEAL | MONIFC | GLOMCI |
|---|---|---|---|---|---|---|
| 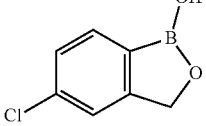 | 201 | 3.8 | 29.5 | 16.1 | 8.5 | 9.3 |

BOTRCI = *Botrytis cinerea* (gray mold)
PENIEX = *Penicillium expansum* (blue mold of apple)
ALTEAL = *Alternaria alternata* (brown spot of tobacco)
MONIFC = *Monilinia fructicola* (brown rot of apple)
GLOMCI = *Glomerella cingulata* (anthracnose of pepper)

Example 9

12-Well (6.5 mL volume per well) microtiter plates are used for the in vitro inhibition assay for volatile antimicrobial compounds. A 3-mL volume of full-strength Potato Dextrose Agar (PDA) is added to each well. After cooling, 1 µL of 1×10$^5$ per mL *Botrytis cinerea* and *Penicillium expansum* spore suspension is spot-pipetted to the center of the agar. Plates are inoculated immediately prior to volatile fungicide treatment. A Whatman #1 filter disk (Cat. No. 1001-0155) is placed, in duplicate, on the underside of a polyethylene PCR plate sealing film. For determination of the minimum inhibitory concentration (MIC), compounds are diluted in acetone, and the appropriate amount of compound is added to the disks in a dose dependent manner to achieve a final headspace concentration of 35.7 to 0.03 mg/L. The acetone is permitted to evaporate for 5 minutes. The headspace around the inoculum is then sealed inside the well by the film with the adhering disk containing the fungicide by inverting the plates over the treated disks and sealing to prevent any of the chemical from flaking from the disk and falling onto the inoculated agar. After 3 days of storage at 23° C., the cultures are evaluated for percent growth relative to control based on measurement of fungal colony diameter. Experimental results are summarized in Table 8. The results indicate that numerous benzoxaborole compounds have excellent in vitro activity against two selected plant fungal pathogens.

TABLE 8

MIC (mg/L) of numerous benzoxaborole compounds applied as a volatile treatment against *Botrytis cinerea* and *Penicillium expansum* plant fungal pathogens.

| Structure | Cmpd # | BOTRCI | PENIEX |
|---|---|---|---|
| 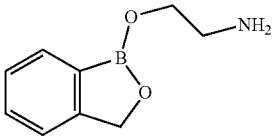 [SMILES: NCCOB1OCc2ccccc21] | 21 | 1.1 | 35.7 |
| 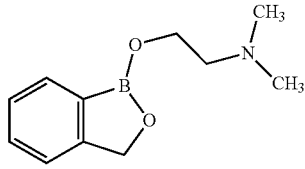 | 22 | 4.5 | 35.7 |
| 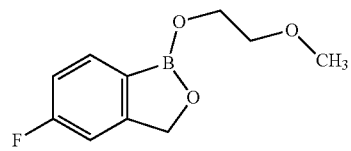 | 38 | 0.6 | 8.9 |

TABLE 8-continued

MIC (mg/L) of numerous benzoxaborole compounds applied as a volatile treatment against *Botrytis cinerea* and *Penicillium expansum* plant fungal pathogens.

| Structure | Cmpd # | MIC (mg/L) BOTRCI | MIC (mg/L) PENIEX |
|---|---|---|---|
| 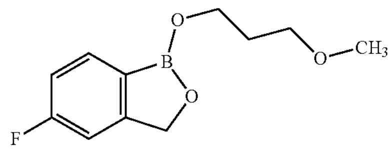 [SMILES: COCCCOB1OCc2cc(F)ccc21]  | 39 | 0.6 | 8.9 |
| 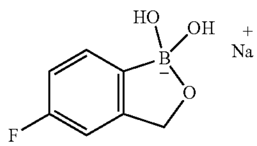  | 54 | 0.6 | 4.5 |
| 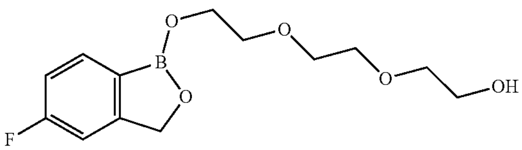 [SMILES: OCCOCCOCCOB1OCc2cc(F)ccc21]  | 55 | 4.5 | >35.7 |
| 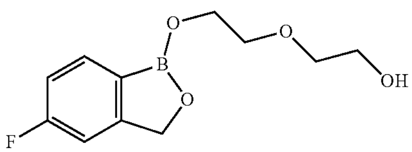 [SMILES: OCCOCCOB1OCc2cc(F)ccc21]  | 62 | 2.2 | 8.9 |
| 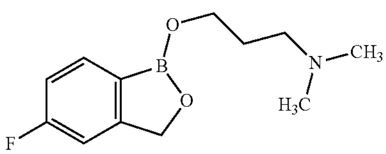 [SMILES: CN(C)CCCOB1OCc2cc(F)ccc21]  | 63 | 1.1 | 17.9 |
| 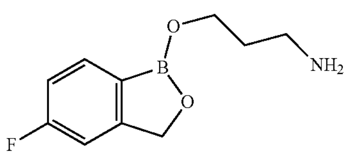 [SMILES: NCCCOB1OCc2cc(F)ccc21]  | 64 | 1.1 | 8.9 |
| 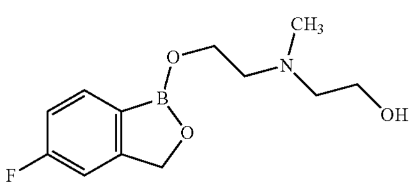 [SMILES: CN(CCO)CCOB1OCc2cc(F)ccc21]  | 72 | 35.7 | >35.7 |
| 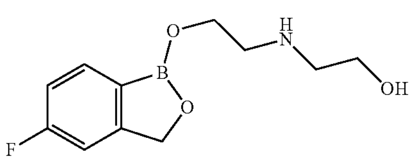 [SMILES: OCCNCCOB1OCc2cc(F)ccc21]  | 73 | 35.7 | >35.7 |
| 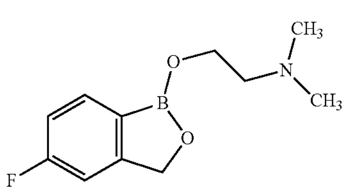 [SMILES: CN(C)CCOB1OCc2cc(F)ccc21]  | 74 | 2.2 | 35.7 |

TABLE 8-continued
MIC (mg/L) of numerous benzoxaborole compounds applied as a volatile treatment against *Botrytis cinerea* and *Penicillium expansum* plant fungal pathogens.
| Structure | Cmpd # | MIC (mg/L) BOTRCI | MIC (mg/L) PENIEX |
|---|---|---|---|
| 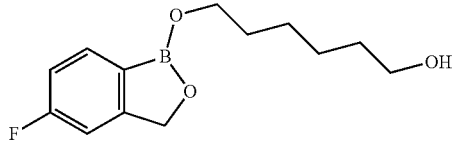 [SMILES: OCCCCCCOB1OCc2cc(F)ccc21] | 86 | 0.6 | 8.9 |
| 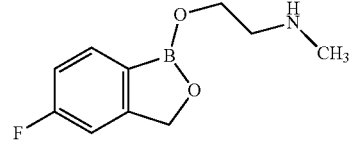 | 87 | 0.6 | 8.9 |
| 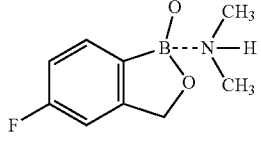 | 105 | 0.6 | 4.5 |
| 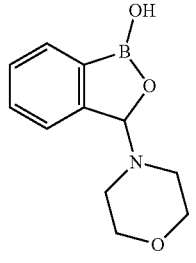 [SMILES: OB1OC(N2CCOCC2)c2ccccc21] | 114 | 17.9 | >35.7 |
| 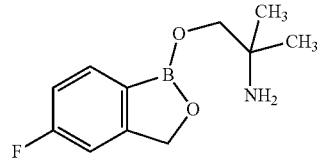 [SMILES: CC(C)(N)COB1OCc2cc(F)ccc21] | 115 | 0.6 | 8.9 |
| 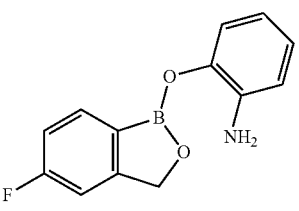 [SMILES: Nc1ccccc1OB1OCc2cc(F)ccc21] | 116 | 1.1 | 8.9 |
| 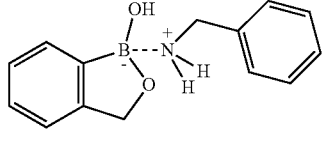 | 121 | 4.5 | 17.9 |
| 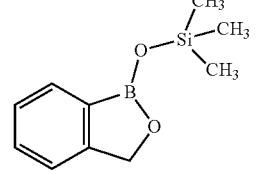 | 122 | 2.2 | 17.9 |

TABLE 8-continued
MIC (mg/L) of numerous benzoxaborole compounds applied as a volatile treatment against *Botrytis cinerea* and *Penicillium expansum* plant fungal pathogens.
| Structure | Cmpd # | MIC (mg/L) BOTRCI | MIC (mg/L) PENIEX |
|---|---|---|---|
| 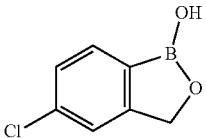 [SMILES: OB1OCc2cc(Cl)ccc21] | 124 | 4.5 | 8.9 |
| 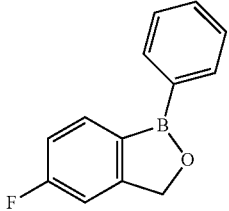 [SMILES: Fc1ccc2c(c1)COB2c1ccccc1] | 127 | 2.2 | 4.5 |
| 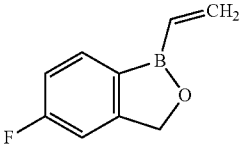 | 129 | 4.5 | 8.9 |
| 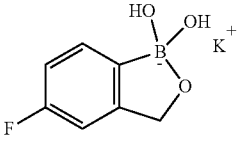 | 130 | 1.1 | 4.5 |
| 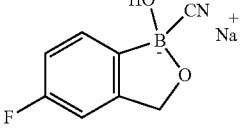 | 132 | 1.1 | 4.5 |
| 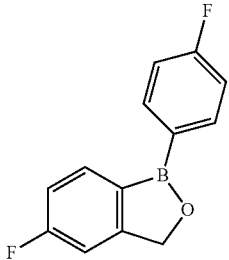 [SMILES: Fc1ccc(B2OCc3cc(F)ccc32)cc1] | 133 | 8.9 | 35.7 |
| 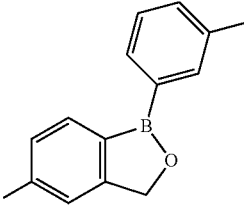 | 134 | 17.9 | >35.7 |

TABLE 8-continued

MIC (mg/L) of numerous benzoxaborole compounds applied as a volatile treatment against *Botrytis cinerea* and *Penicillium expansum* plant fungal pathogens.

| Structure | Cmpd # | MIC (mg/L) BOTRCI | PENIEX |
|---|---|---|---|
| 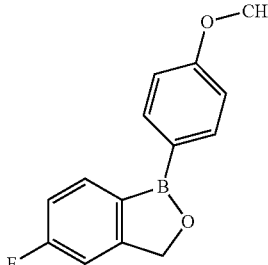 | 135 | 17.9 | >35.7 |
| 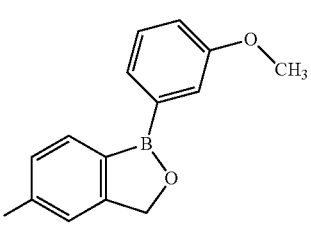 | 136 | 8.9 | >35.7 |
| 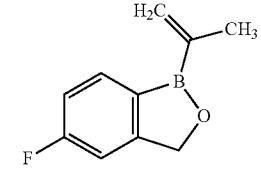 | 137 | 0.3 | 1.1 |
| 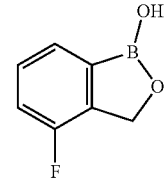 | 202 | 35.7 | 142.9 |
| 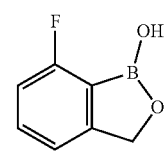 | 203 | 8.9 | 142.9 |
| 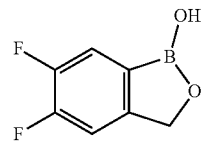 | 204 | 8.9 | >35.7 |

BOTRCI = *Botrytis cinerea* (gray mold)
PENIEX = *Penicillium expansum* (blue mold of apple)

Example 10

12-Well (6.5 mL volume per well) microtiter plates are used for the in vitro inhibition assay for volatile antimicrobial compounds A and B (FIG. 1) against numerous plant fungal pathogens. A 3-mL volume of full-strength Potato Dextrose Agar (PDA) is added to each well. After cooling, 1 µL of 1×10$^5$ spores per mL of *Botrytis cinerea*, *Penicillium expansum*, *Alternaria alternata*, *Glomerella cingulata*, *Penicillium digitatum*, *Monilinia fruticola*, *Aspergillus brasiliensis*, *Colletotrichum acutatum*, *Fusarium sambucinum*, *Phytophthora capsici*, *Geotrichum candidum*, *Aspergillus niger*, *Diplodia gossypina* or *Diaporthe citrii* suspension is spotted onto the center of the agar. A Whatman #1 filter disk (Cat. No. 1001-0155) is placed, in duplicate, on the underside of a polyethylene PCR plate sealing film. For determination of the minimum inhibitory concentration (MIC), test compounds are diluted in acetone, and the appropriate amount of compound is added to the disks in a dose dependent manner to achieve a final headspace concentration of 35.7 to 0.03 mg/L. The acetone is permitted to evaporate for five minutes. The headspace around the inoculum is then sealed inside the well by the film with the adhering disk containing the fungicide by inverting the plates over the treated disks and sealing to prevent any of the chemical from flaking from the disk and falling onto the inoculated agar. After 3 days of storage at 23° C., cultures are evaluated for percent growth relative to control. Results shown in Table 9 demonstrate the ability of benzoxaborole compounds A and B to control the growth of numerous fungal plant pathogens through volatile activity.

TABLE 9

MIC (mg/L) of Compounds A and B applied as a volatile against numerous fungal plant pathogens

| Pathogens | Compound A MIC | Compound B MIC |
|---|---|---|
| B. cinerea | 2.2 | 4.5 |
| P. expansum | 1.1 | 8.9 |
| M. fruticola | 2.2 | 1.1 |
| A. alternata | 2.2 | 2.2 |
| G. cingulata | 17.9 | 35.7 |
| P. digitatum | 2.2 | 4.5 |
| A. brasiliensis | 2.2 | 0.6 |
| C. acutatum | 4.4 | 8.9 |
| F. sambucinum | 1.1 | 4.5 |
| P. capsici | 1.1 | n/a |
| G. candidum | 8.9 | 8.9 |
| A. niger | 2.2 | 1.1 |
| M. piriformis | 1.1 | 2.2 |
| D. gossypina | 1.1 | 4.5 |
| D. citrii | 2.2 | 17.9 |

Example 11

12-Well (6.5 mL volume per well) microtiter plates are used for the in vitro inhibition assay for volatile antimicrobial Compound A (FIG. 1) against numerous bacterial pathogens. A 3-mL volume of Nutrient agar is added to each well and allowed to dry before introducing the pathogen. Escherichia coli, Pectobacterium carotovorum, Xanthomonas axonopodis and Salmonella enterica cell suspensions are adjusted to an optical density of 0.2 to 0.35, and further diluted 1/10, and 15 µL is pipetted to the center of each well and tilted to distribute uniformly. A Whatman #1 filter paper (CAT 1001-0155) is placed on the underside of a polyethylene PCR plate sealing film. For determination of minimum bactericidal concentration (MBC), Compound A is diluted in acetone, and 50 µL are applied to the disks, in duplicate, in a dose dependent manner in order to achieve a final headspace concentration of 71.4 to 0.03 mg/L. The acetone is permitted to evaporate for 5 minutes. The films with the treated disks are then applied over the inoculated plates and sealed. Plates are inverted, and incubated at 23° C. for 48 hours. After the incubation period, the bacteria colonies are dislodged in sterile water containing tween 80 (0.001%) and the optical density (OD; 600 nm) is determined Results are summarized in Table 10, where the headspace concentration required to control at least 80% of bacterial growth is reported. Compound A shows good antimicrobial activity against numerous bacteria in this in vitro assay.

TABLE 10

Rate (mg/L) of Compound A offering at least 80% control against bacterial pathogens

| E. coli | P. carotovorum | X. axonopodis | S. enterica |
|---|---|---|---|
| 35.7 | 2.2 | 4.5 | 17.9 |

Example 12

In order to assess the in vivo activity of volatile antimicrobial Compound A, a volatile bioassay is developed to evaluate the control of Escherichia coli and Salmonella enterica on fresh beef. The beef is washed to remove any natural inoculum by rinsing in warm water for 2 minutes. Two strips, single layer, are placed in a sterile 10.8-cup SnapWare airtight container (Model #109842).

TABLE 11

Colony forming unit (CFU/mL) and log reductions of E. coli and S. enterica from beef after a volatile treatment with Compound A.

| Pathogens | Treatments | Log CFU/mL | Log reduction |
|---|---|---|---|
| E. coli | Control | 8.27 | 3.17 |
|  | Compound A | 5.09 |  |
| S. enterica | Control | 7.38 | 2.43 |
|  | Compound A | 4.95 |  |

Each strip is inoculated on the surface by placing 20 µL of either E. coli or S. enterica cell suspensions that are adjusted to an optical density of 0.35 (600 nm), and further diluted 1/10. For determination of efficacy, Compound A powder is introduced into the container with a sublimation device (copper tube heated to 200° C. with fan flow at 0.5 liters per minute (L/min)) at a rate required to achieve a final headspace concentration of 100 mg/L. The containers and their contents are then incubated for 2 days at 21° C. After treatment, the beef is washed, and the wash is collected, serially diluted, plated on nutrient agar, and then incubated for an additional 24 hours at 37° C. Bacterial colonies are counted and expressed as colony forming units (CFU/mL), with the log reduction calculated relative to the control. Results listed in Table 11 show good antimicrobial activity of Compound A against E. coli and S. enterica in this in vivo assay using beef. Compound A demonstrates a 3.17 log reduction (>99.9%) of E. coli and a 2-log reduction for S. enterica.

Example 13

In order to assess the in vivo activity of volatile antimicrobial Compound A on controlling Botrytis cinerea on ornamental flowers, a volatile bioassay is developed using white carnations.

TABLE 12

Botrytis cinerea incidence on carnations treated with Compound A

| Compound A | Disease incidence (%) on Petals | | | | |
|---|---|---|---|---|---|
| Rates (mg/L) | Day 0 | Day 1 | Day 2 | Day 3 | Day 8 |
| 1 | 0 | 0 | 0 | 4 | 16 |
| 0.2 | 0 | 8 | 20 | 16 | 36 |

TABLE 12-continued

Botrytis cinerea incidence on carnations treated with Compound A

| Compound A Rates (mg/L) | Disease incidence (%) on Petals | | | | |
|---|---|---|---|---|---|
| | Day 0 | Day 1 | Day 2 | Day 3 | Day 8 |
| 0.04 | 0 | 0 | 16 | 40 | 92 |
| Control | 0 | 68 | 92 | 96 | 100 |

Five carnations are placed in an 800 mL jar containing 200 mL of a common commercial flower preservative. Five jars are then placed in a 117 L Rubbermaid storage box (Cat #2244). The petals are uniformly spray-inoculated with 5 mL of $1\times10^5$ spores/mL of Botrytis cinerea suspension. The tub is closed tightly. For treatment application, Compound A is dissolved in an aqueous 1,2-propylene glycol solution (3:1) and 5 mL of the solution is volatilized into the container using an ES-100-H SmartFog system (Reno, Nev.) through a ½" side port that is sealed immediately after the application. The flowers are incubated for 3 days at 21° C. After storage, the flowers are evaluated for incidence based on presence of disease on flower petals relative to untreated control flowers for up to 8 days at 21° C., with results summarized in Table 12. Compound A at 1 mg/L shows 0% incidence 2 days after treatment removal and only 16% incidence after 8 days, and generally demonstrates good volatile antimicrobial activity against Botrytis cinerea in this in vivo analysis of infection in an ornamental flower.

Example 14

A similar test like the one described above is also performed on white carnations (treated with or without the commercial anti-ethylene compound silver thiosulfate; STS) with natural inoculum. Compound A is either dissolved in an aqueous 1,2-propylene glycol solution (3:1) and 5 mL of the solution volatilized using an ES-100-H SmartFog system (Reno, Nev.) through a ½" side port that is sealed immediately after the application, or dissolved in acetone and applied to a 42.5 millimeter (mm) Whatman #1 filter disk (Cat. No. 1001-042), and placed on a watch glass after allowing the acetone to evaporate for 5 minutes. The flowers are incubated for 3 days at 21° C. After storage, the flowers are evaluated for an additional 8 days for disease severity based on the number of lesions present on flower petals and sepals. Results listed in Table 13 show good antimicrobial activity against Botrytis cinerea in this in vivo analysis.

TABLE 13

Botrytis cinerea severity after 8 days of shelf-life based on number of lesions on petals and sepals after an active fog or passive volatile treatment with Compound A.

| | Compound A | Severity (Average Number of Lesions) | | | |
|---|---|---|---|---|---|
| | | Non-STS | | STS | |
| Plant Part | Rate (mg/L) | Fog | Volatile | Fog | Volatile |
| Petals | 1 | 0 | 1.5 | 0 | 0.1 |
| | 0.2 | 0 | 1.8 | 0 | 0.1 |
| | 0.04 | 0.4 | 3.1 | 0.3 | 0.5 |
| | 0 | 2.1 | 18.8 | 7.7 | 43.2 |
| Sepals | 1 | 0.04 | 1 | 0.04 | 0.2 |
| | 0.2 | 0.04 | 1.6 | 0.1 | 0.3 |
| | 0.04 | 0.3 | 2.1 | 0.6 | 1.1 |
| | 0 | 4.5 | 4.8 | 6.8 | 3.6 |

Example 15

A similar test like the one described above is also performed on white roses with natural inoculum. Five white roses are placed in an 800 mL jar containing 200 mL of a common commercial flower preservative.

TABLE 14

Botrytis cinerea incidence and severity based on infection on petals and sepals of white roses after a three day volatile treatment of Compound A at 21° C., and an additional two days at 21° C.

| | Applied through sublimation | | Volatilized from Whatman Filter | |
|---|---|---|---|---|
| Compound A Rate (mg/L) | Incidence (%) | Severity (0-4)* | Incidence (%) | Severity (0-4)* |
| 1 | 0 | 0 | 53.3 | 1.6 |
| 0.2 | 13.3 | 0.5 | 66.7 | 1.8 |
| 0.04 | 46.7 | 1.7 | 46.7 | 1.1 |
| Control- Acetone | 80 | 2.9 | 86.7 | 2.4 |
| Control | 100 | 3.1 | 100 | 3.1 |

*Severity Rating
0 = No disease
1 = Browning and small lesions on the sepals or petals
2 = Browning, petals covered with fungal spores
3 = Browning, petals covered with fungal spores, some petal drop
4 = Browning, petals covered with fungal spores, some flowers aborted Three jars are then placed in a 117 L Rubbermaid storage box (Cat #2244). Two small fans are place in opposite ends of the container to assist with the volatile distribution of compound A. The tub is closed tightly, and then Compound A is diluted in acetone, and then pipetted onto a 1.5 inch×1 inch cotton strip. The acetone is allowed to evaporate for five minutes. Compound A is then introduced to the containers by a sublimation device (copper tube heated to 200° C. with fan flow at 0.5 L/min) to achieve a final headspace concentration of 0.04, 0.2, 1 mg/L, through a ½" side port that is sealed immediately after the application. Alternatively, Compound A is pipetted onto a 42.5 mm Whatman #1 filter disk (Cat. No. 1001-042), supported by a watch glass, where the acetone is allowed to evaporate for five minutes prior to sealing the container. The flowers are incubated for three days at 21° C. After treatment, flowers are evaluated for an additional two days for disease incidence and severity of the flower petals. Applying a treatment at 1 mg/L through sublimation results in 0% incidence. Rose petals after treatment with Compound A have no disease incidence, retained white color, and the roses had no petal drop. Results listed in Table 14 show good antimicrobial activity against Botrytis cinerea infection of white roses, and that enhancing the rate of volatilization through sublimation resulted in greater disease control.

Example 16

To test the effect of Compound A (FIG. 1) on vegetables, potato, onion and squash were obtained from a local store, and the surface sterilized with 0.825% sodium hypochlorite (NaOCl). A slice of potato or two leaves of onion were placed in a sterile Petri plate, while whole squash were placed in a sterile 10.8-cup SnapWare airtight container (Model #109842). Each slice of potato was inoculated with 20 µL of a $1\times10^5$ spores/mL Fusarium sambucinum suspension, while onions were inoculated with 20 µL of a $1\times10^6$ spores/mL Botrytis cinerea suspension. For inoculation of squash, a small core was removed, and a mycelial plug of Phytophthora capsici was inserted and capped with the core.

Compound A was diluted in acetone, and added to a 42.5 mm Whatman #1 filter disk (Cat. No. 1001-042) attached to the inner side of the lid at a rate to achieve a final headspace concentration of 10 mg/L. The acetone was permitted to evaporate for 5 minutes before parafilm sealing the plates or closing the airtight containers. The vegetables were incubated at 21° C. for 3 days, and evaluated for mycelial growth, dry rot, and water-soaked appearance (mm diameter) with results summarized in Table 13. Compound A demonstrated good fungal control of 3 plant pathogens using 3 different vegetable crops in this in vivo assay.

TABLE 15

Effect of Compound A at controlling fungal growth on potato, onion and squash.

| Treatments | Potato *Fusarium sambucinum* | | Onion *Botrytis cinerea* | Squash *Phytophthora capsici* | |
| --- | --- | --- | --- | --- | --- |
| | Mycelial growth | Dry rot | Water soaked | Water soaked | Mycelial growth |
| 10 mg/L | 0 | 0 | 0 | 5.3 | 1.1 |
| Control-acetone | 4.3 | 4.7 | 7 | 24 | 17.4 |
| Control-no acetone | 31.6 | 10.3 | 8.5 | 30.9 | 24.7 |

Example 17

To test the effect of Compound A at controlling bacterial pathogens of vegetables, potato, onion and carrot are chopped into small cubes and surface sterilized with 0.825% NaOCl and allowed to dry. Four small cubes (approximately 1 square centimeter ($cm^2$)) of each vegetable are placed in a sterile Petri plate. Each cube is inoculated with 25 μL of *Pectobacterium carotovorum* (bacterial concentration of OD 1.0, 600 nm). For determination of efficacy, Compound A is diluted in acetone, and the appropriate volume to achieve a final headspace concentration of 50 mg/L is added to a 42.5 mm Whatman #1 filter disk (Cat. No. 1001-042) attached to the inner side of the lid. The acetone is permitted to evaporate for five minutes before closing the plate and sealing it with parafilm. The vegetables are incubated at 10 C for four days. Results listed in Table 16 demonstrate antimicrobial activity against *P. carotovorum* on onion (2.14 log reduction), carrot (0.29 log reduction) and potato (0.84 log reduction) in this in vivo analysis.

TABLE 16

Effects of Compound A (50 mg/L) in reducing growth of *P. carotovorum* on potato, onion and carrot.

| Crops | Treatments | Log CFU/mL | Log reduction |
| --- | --- | --- | --- |
| Potato | Control | 7.47 | |
| | Compound A | 6.63 | 0.84 |
| Onion | Control | 8.13 | |
| | Compound A | 5.99 | 2.14 |
| Carrot | Control | 6.36 | |
| | Compound A | 6.06 | 0.29 |

Example 18

In order to assess the in vivo activity of volatile antimicrobial Compound A in fruit, a volatile bioassay is developed using strawberry, grape and blueberry. Eight strawberries, 16 grapes or 30 blueberries (per replicate) are placed in a commercially relevant sized PET clamshell, with the stem end facing up for blueberries and grapes, and downwards for strawberries. A fresh wound is inoculated with 20 μL (strawberry and grape) or 10 μL (blueberry) of $1 \times 10^6$ per mL *Botrytis cinerea* spore suspension. The clamshells are placed inside a 10.8-cup SnapWare airtight container (Model #109842). A 42.5 mm Whatman #1 filter disk (Cat. No. 1001-042) is placed on a watch glass. Compound A is dissolved in acetone and added to the disks in a dose dependent manner to produce a final headspace concentration of 0.4, 2, or 10 mg/L. The acetone is permitted to evaporate for five minutes. The containers are then closed with lids and placed for three days at 21° C. After storage, fruits are evaluated for incidence and severity (0 to 4) of disease for an additional three days at 21° C., with results summarized in Table 17. Results demonstrate good in vivo volatile antimicrobial control of *Botrytis cinerea* with approximately 50% lower incidence and dramatically lower severity for strawberry, grape and blueberry after three days of shelf-life.

TABLE 17

Effect of a three day volatile treatment of Compound A (0.4, 2 or 10 mg/L) in controlling the incidence and severity of *B. cinerea* infection of strawberry, grape and blueberry during a 3three day post-treatment evaluation period at 21° C.

| | | Strawberry | | Grape | | Blueberry | |
| --- | --- | --- | --- | --- | --- | --- | --- |
| Compound A Rate (mg/L) | Evaluation Days | Incidence (%) | Severity (0-4) | Incidence (%) | Severity (0-4) | Incidence (%) | Severity (0-4) |
| 10 | 0 | 7.1 | 0 | 0 | 0 | 12.9 | 0.1 |
| 2 | 0 | 14.3 | 0.1 | 0 | 0 | 9.7 | 0 |
| 0.4 | 0 | 0 | 0 | 3.1 | 0 | 21 | 0.1 |
| Control | 0 | 50 | 0.4 | 100 | 2.3 | 95.2 | 1.2 |
| 10 | 1 | 35.7 | 0.2 | 0 | 0 | 12.9 | 0.1 |
| 2 | 1 | 50 | 0.3 | 0 | 0 | 9.7 | 0 |
| 0.4 | 1 | 21.4 | 0.1 | 3.1 | 0 | 21 | 0.2 |
| Control | 1 | 100 | 1 | 100 | 2.5 | 100 | 1.7 |

TABLE 17-continued

Effect of a three day volatile treatment of Compound A (0.4, 2 or 10 mg/L) in controlling the incidence and severity of B. cinerea infection of strawberry, grape and blueberry during a 3three day post-treatment evaluation period at 21° C.

| Compound A Rate (mg/L) | Evaluation Days | Strawberry Incidence (%) | Strawberry Severity (0-4) | Grape Incidence (%) | Grape Severity (0-4) | Blueberry Incidence (%) | Blueberry Severity (0-4) |
|---|---|---|---|---|---|---|---|
| 10 | 2 | 42.9 | 0.5 | 3.1 | 0 | 12.9 | 0.2 |
| 2 | 2 | 50 | 0.3 | 0 | 0 | 9.7 | 0.1 |
| 0.4 | 2 | 21.4 | 0.1 | 15.6 | 0.2 | 40.3 | 0.5 |
| Control | 2 | 100 | 2.2 | 100 | 2.7 | 100 | 1.9 |
| 10 | 3 | 42.9 | 0.8 | 56.3 | 0.4 | 41.9 | 0.6 |
| 2 | 3 | 64.3 | 0.5 | 56.3 | 0.3 | 40.3 | 0.6 |
| 0.4 | 3 | 28.6 | 0.5 | 62.5 | 0.5 | 62.9 | 1 |
| Control | 3 | 100 | 2.7 | 100 | 3.8 | 100 | 2.1 |

*Severity
0 = no fungal growth
1 = slight infection (only visible inside wound with microscope)
2 = moderate infection (visible growth at the point of inoculation)
3 = high infection (>1 cm diameter cone of Botrytis)
4 = extreme infection (>half-length of fruit)

Example 19

In order to assess the in vivo activity of volatile antimicrobial Compound A in fruit, a volatile bioassay is developed using orange fruit. Two oranges are placed inside a PET clamshell. Three fresh wounds per orange are inoculated with 30 μL of 1×10$^6$ per mL *Penicillium digitatum* spore suspension. The clamshells are placed inside a 10.8-cup SnapWare airtight container (Model #109842). A 42.5 mm Whatman #1 filter disk (Cat. No. 1001-042) is placed on a watch glass. Compound A is dissolved in acetone and added to the disks in a dose dependent manner to produce a final headspace concentration of 2, 10, or 50 mg/L. The acetone is permitted to evaporate for five minutes. The containers are then closed with the lids and placed for three days at 21° C. After storage, fruits are evaluated for disease incidence (mm diameter of the rot) and pathogen sporulation (mm diameter) on the surface of the fruits for an additional two days at 21° C., with results summarized in Table 18. Results demonstrate good in vivo volatile antimicrobial control of *P. digitatum* in inoculated orange, especially at rates greater than 10 mg/L.

TABLE 18

Incidence and severity of *Penicillium digitatum* on oranges as depicted by water soaked lesion and fungal spores on the surface of the fruits

| Compound A Rate (mg/L) | Water soaked Lesions (mm) | | | Sporulation (mm) | | |
|---|---|---|---|---|---|---|
| | Day 0 | Day 1 | Day 2 | Day 0 | Day 1 | Day 2 |
| 50 | 0 | 0 | 5 | 0 | 0 | 1.2 |
| 10 | 0 | 0 | 9 | 0.5 | 0.4 | 2.5 |
| 2 | 0 | 0 | 13.4 | 0 | 0.4 | 2.7 |
| Control | 17.8 | 31.2 | 52.4 | 5 | 15.1 | 35.6 |

Example 20

In order to assess the in vivo activity of volatile antimicrobial Compound A in fruit, a volatile bioassay is developed using apple. Two apples are placed inside a PET clamshell. Three fresh wounds per apple are inoculated with 30 μL of 1×10$^6$ per mL *Penicillium expansum* spore suspension. The clamshells are placed inside a 10.8-cup SnapWare airtight container (Model #109842). A 42.5 mm Whatman #1 filter disk (Cat. No. 1001-042) is placed on a watch glass. Compound A is dissolved in acetone and added to the disks in a manner to produce a final headspace concentration of 50 mg/L. The acetone is permitted to evaporate for five minutes. The containers are then closed with the lids, and placed for three days at 21° C. After storage, fruits are evaluated for disease incidence (mm diameter of the rot) and pathogen sporulation (mm diameter) on the surface of the fruits for an additional three days at 21° C., with results summarized in Table 19. Results demonstrate 100% in vivo volatile antimicrobial control of *P. expansum* mold of apple up to 3 days after treatment.

TABLE 19

Incidence and severity of *Penicillium expansum* on apples as depicted by a brown rot and fungal spores on the surface of the fruits

| Compound A Rate (mg/L) | Rot (mm) | | | | Sporulation (mm) | | | |
|---|---|---|---|---|---|---|---|---|
| | Day 0 | Day 1 | Day 2 | Day 3 | Day 0 | Day 1 | Day 2 | Day 3 |
| 50 | 0 | 0 | 0 | 0 | 0 | 0 | 0 | 0 |
| Control | 15.9 | 20.1 | 25.7 | 30 | 3.5 | 3.9 | 3.9 | 6.5 |

Example 21

In order to assess the in vivo activity of volatile antimicrobial Compound B in fruit, a volatile bioassay is developed using orange. Two oranges per replicate are placed inside a clamshell. Three fresh wounds per orange are inoculated with 30 μL of 1×10$^6$ per mL *Penicillium digitatum* spore suspension. The clamshells are placed inside a 10.8-cup SnapWare airtight container (Model #109842). Compound B powder is introduced to the containers by a sublimation device (copper tube heated to 200° C. with fan flow at 0.5 L/min) to achieve a final headspace concentration of 0.4, 2, 10, or 50 mg/L. The containers are then closed with the lids and placed for three days at 21° C. After storage, fruits are evaluated for disease incidence (mm diameter of the rot) and pathogen sporulation (mm diameter) on the surface of the fruits for an additional three days at 21° C., with results summarized in Table 20. Results demonstrate good in vivo volatile inhibition of *P. digitatum* in orange at rates of 0.4 mg/L and complete inhibition at 10 mg/L.

fruits except for strawberry (stem end facing downwards). A fresh wound is inoculated with 20 μL 1×10$^6$ per mL *Penicillium expansum* spore suspension (apple and pear), 20 μL 1×10$^6$ per mL *Penicillium digitatum* spore suspension (orange), and 20 μL (strawberry and grape) or 10 μL (blueberry) of 1×10$^6$ per mL *Botrytis cinerea* spore suspension. The clamshells are placed inside a 117 L Rubbermaid storage box (Cat #2244) with lids closed. Compound A, dissolved in acetone, is pipetted onto a cotton strip, where the acetone is allowed to evaporate for five minutes, and then introduced into the container by a sublimation device (copper tube heated to 200° C. with fan flow at 0.5 L/min) to achieve a final headspace concentration of 10 mg/L. The containers are then held for three days at 21° C. After treatment, fruits are held for an additional three days at 21° C., then evaluated for disease incidence (mm diameter of browning or water-soaked lesions) and pathogen sporulation (mm diameter) for apple, pear and orange, as well as *Botrytis cinerea* disease incidence (%) and severity (0 to 4) for strawberry, grape and blueberry, with results summarized in Table 21. Results demonstrate good in vivo antimicrobial control of at least three fungal pathogens on at least six different hosts when applied as a volatile fungicide.

TABLE 20

Incidence and severity of *Penicillium digitatum* on oranges as depicted by water soaked lesion and fungal spores on the surface of the fruits after a treatment with Compound B.

| Compound B | Water soaked lesions (mm) | | | | Sporulation (mm) | | | |
|---|---|---|---|---|---|---|---|---|
| Rate (mg/L) | Day 0 | Day 1 | Day 2 | Day 3 | Day 0 | Day 1 | Day 2 | Day 3 |
| 50 | 0 | 0 | 0 | 0 | 0 | 0 | 0 | 0 |
| 10 | 0 | 0 | 0 | 0.8 | 0 | 0 | 0 | 0 |
| 2 | 0.5 | 7.8 | 30.7 | 42.6 | 0 | 0.3 | 2.8 | 5.7 |
| 0.4 | 5.7 | 29.4 | 49.3 | 63.4 | 0.7 | 1.4 | 8.1 | 27.2 |
| Control | 12.3 | 35.5 | 61.1 | 83.2 | 0.3 | 2.7 | 8.5 | 44.5 |

Example 22

To assess the in vivo activity of volatile antimicrobial Compound A (FIG. 1) in fruit, a volatile bioassay is developed using apple, pear, orange, strawberry, grape and blueberry. Two apples, 2 oranges, 2 pears, 8 strawberries, 16 grapes or 30 blueberries (per replicate, in duplicate) are placed in a clamshell with the stem end facing up for all

TABLE 21

Effects of subliming Compound A as reflected by incidence and severity of *B. cinerea* on strawberry, grape and blueberry, and severity on oranges, apples and pears as depicted by water soaked lesions, browning and sporulation after a three day treatment plus an additional three days at 21° C.

| Treatment | Incidence (%) | | | Severity (0-4) | | |
|---|---|---|---|---|---|---|
| (10 mg/L) | Strawberry | Blueberry | Grape | Strawberry | Blueberry | Grape |
| Compound A | 18.8 | 5 | 26.7 | 0.09 | 0.03 | 0.1 |
| Control | 100 | 100 | 80 | 3.6 | 2.2 | 0.9 |

| | Water soaked lesion | Browning (mm) | | Sporulation (mm) | | |
|---|---|---|---|---|---|---|
| | Orange | Apple | Pear | Apple | Orange | Pear |
| Compound A | 3.04 | 5.4 | 2.7 | 0 | 8.55 | 0 |
| Control | 50.5 | 11.5 | 23.3 | 4.8 | 33.2 | 15.5 |

Example 23

To compare the ability of Compound A when actively volatilized by different mechanisms, an in vivo assay using strawberry is performed. Eight strawberries are placed in a clamshell with stem end facing downwards. A fresh wound is inoculated with 20 μL of 1×10$^5$ per mL *Botrytis cinerea* spore suspension. The clamshell is placed in a 10.8-cup SnapWare airtight container (Model #109842) and closed with the lids. Compound A is dissolved in acetone and volatilized through a sealable ½ inch side port by an ES-100-H SmartFog system (Reno, Nev.). Alternatively, Compound A, dissolved in acetone, is pipetted onto a cotton strip, where the acetone is allowed to evaporate for five minutes, and then introduced into the container by a sublimation device (copper tube heated to 200° C. with fan flow at 0.5 L/min) to achieve a final headspace concentration of 10 mg/L. The fruits are stored for three days at 21° C. After the three days of treatment, fruit are stored for an additional three days at 21° C., and then evaluated for incidence (%) and severity of disease (0 to 4). Results are summarized in Table 22 and demonstrate good antimicrobial activity against *Botrytis cinerea* in this in vivo analysis, indicating that Compound A is an effective volatile antimicrobial.

TABLE 22

Effects of different volatile application methods of Compound A as reflected by incidence and severity of *Botrytis cinerea* on strawberry after a three day treatment plus an additional three days at 21° C.

| Treatments | Incidence (%) | Severity (0 to 4) |
| --- | --- | --- |
| Fog, 10 mg/L Compound A | 6.3 | 0.03 |
| Fog, control | 62.5 | 1.6 |
| Sublimation, 10 mg/L Compound A | 0.0 | 0.0 |
| Sublimation, control | 100.0 | 3.7 |

Example 24

An in vivo assay is used to evaluate the ability of Compound A to volatilize from different materials and control fungal pathogens. Eight strawberries are placed in a clamshell with stem end facing downwards. A fresh wound is inoculated with 20 μL of 1×10$^6$ per mL *Botrytis cinerea* spore suspension. The clamshells are then placed in a 10.8-cup SnapWare airtight container (Model #109842). Compound A is dissolved in acetone and then evenly sprayed onto cellulose paper and Tyvek® fabric at a rate of 200 milligrams per square meter (mg/m$^2$). The acetone is allowed to evaporate. Likewise Compound A is dissolved in propylene glycol and evenly sprayed onto cellulose paper and Tyvek® fabric. No evaporation is attempted in this case. Pieces of material are cut to the appropriate dimensions to deliver a final headspace concentration of 0.4, 2, or 10 mg/L. The containers are close, and placed for three days at 21° C. After treatment, fruit are stored for an additional two days at 21° C. and then evaluated for incidence (%) and severity (0 to 4) of disease, with the results summarized in Table 23. Results demonstrate good in vivo antimicrobial activity of Compound A against *Botrytis cinerea*, with a reduction in incidence and severity at all rates, in a dose dependent manner, and that the volatile compound can be released from different materials.

TABLE 23

Effects of different films and subsequent release of Compound A on the incidence and severity of *Botrytis cinerea* on strawberries after a three day treatment and additional two day storage at 21° C.

| Rate (mg/L) | Type of Film | Incidence (%) | Severity (0-4) |
| --- | --- | --- | --- |
| 0.4 | Cellulose Paper | 37.5 | 0.8 |
| 2 | Cellulose Paper | 37.5 | 0.7 |
| 10 | Cellulose Paper | 12.5 | 0.2 |
| 0.4 | Tyvek® | 31.3 | 0.5 |
| 2 | Tyvek® | 6.3 | 0.1 |
| 10 | Tyvek® | 6.3 | 0.3 |
| Control | No film | 100 | 2.5 |

Example 25

An in vivo assay is used to evaluate the ability of Compound A to volatilize from different materials and control fungal pathogens. Eight strawberries are placed in a clamshell with the stem end facing downwards. A fresh wound is inoculated with 20 μL of 1×10$^6$ per mL *Botrytis cinerea* spore suspension. The clamshells are then placed in a 10.8-cup SnapWare airtight container (Model #109842). As a substrate for Compound A, either a 42.5 mm Whatman #1 filter disk (Cat. No. 1001-042) placed on a watch glass or 10 square centimeter (cm$^2$) pieces of cardboard typically used for packaging strawberries was used. Compound A is dissolved in acetone and either pipetted on the disk or painted on the cardboard at a rate to achieve a final headspace concentration of 0.4, 2, or 10 mg/L. The acetone is permitted to evaporate for five minutes. The containers are closed, and placed for three days at 21° C. After treatment, fruit are stored for an additional two days at 21° C. and then evaluated for incidence (%) and severity (0 to 4) of disease, with the results summarized in Table 24. Results demonstrate good in vivo antimicrobial activity of Compound A against *Botrytis cinerea*, with a reduction in incidence and severity at all rates, in a dose dependent manner, and that the volatile compound can be released from different materials.

TABLE 24

Effects of different films and subsequent release of Compound A on the incidence and severity of *Botrytis cinerea* on strawberries after a three day treatment and additional two day storage at 21° C.

| Rate (mg/L) | Type of Material | Incidence (%) | Severity (0-4) |
| --- | --- | --- | --- |
| 10 | Cardboard | 25 | 0.2 |
| 2 | Cardboard | 37.5 | 0.3 |
| 0.4 | Cardboard | 87.5 | 0.9 |
| Control | Cardboard | 93.8 | 2.7 |
| 10 | Filter Paper | 18.8 | 0.3 |
| 2 | Filter Paper | 37.5 | 0.6 |
| 0.4 | Filter Paper | 56.3 | 2.5 |
| Control | Filter Paper | 100 | 2.5 |

Example 26

An in vitro assay is used to evaluate the ability of Compound A (FIG. 1) to volatilize from different materials and control fungal growth.

TABLE 25

Effects of different materials on the volatile release of Compound A
and the subsequent in vitro inhibition (MIC) of *Botrytis cinerea*.

| Material | MIC (mg/L) |
| --- | --- |
| Polyethylene | 0.28 |
| PTFE-Coated Fiberglass | 0.56 |
| Fiberglass | 0.56 |
| Cellulose | 0.56 |
| Silica | 0.56 |
| Aramid and Fiberglass | 0.56 |
| Vinyl-Coated Polyester | 0.56 |
| Acrylic-Coated Fiberglass | 0.56 |
| Silicone-Coated Fiberglass | 0.56 |
| PTFE | 1.1 |
| Cardboard | 2.2 |
| Aramid | 2.2 |

PTFE-Coated (8577K81), Fiberglass (8816k1), Silica (8799K3), Aramid and Fiberglass (8821K4), Vinyl-Coated Polyester (8843K31), Acrylic-Coated Fiberglass (8838K2), Silicone-Coated Fiberglass (87815K1), Aramid (McMaster-Carr, Santa Fe Springs, Calif.-1206T1), Polyethylene PCR sealing film, Cellulose (Whatman #1, Cat No. 1001-0155), and Cardboard are cut into disks of 15 mm diameter. 12-Well (6.5 mL volume per well) microtiter plates are used for the in vitro inhibition assay for volatile antimicrobial compounds. A 3-mL volume of full-strength Potato Dextrose Agar (PDA) is added to each well. After cooling, 1 µL of $1 \times 10^5$ per mL *Botrytis cinerea* spore suspension is spot-pipetted to the center of the agar. Plates are inoculated immediately prior to volatile fungicide treatment. The various materials are placed, in duplicate, on the underside of a polyethylene PCR plate sealing film. For determination of the minimum inhibitory concentration (MIC), compounds are diluted in acetone, and the appropriate amount of compound is added to the materials in a dose dependent manner to achieve a final headspace concentration of 35.7 to 0.03 mg/L. The acetone is permitted to evaporate for five minutes. The headspace around the *Botrytis cinerea* inoculum is then sealed inside the well by the film with the adhering disk of material containing the fungicide. Plates are inverted, placed over the treated disks and sealed to prevent any of the chemical from flaking from the disk and falling onto the inoculated agar. After three days of storage at 23° C., the cultures are evaluated for percent growth relative to control based on measurement of fungal colony diameter. Experimental results are summarized in Table 25. The results indicate that Compound A can volatilize from numerous materials to inhibit the in vitro growth of *Botrytis cinerea* with similar levels of control.

Example 27

An in vivo assay is used to evaluate the ability of Compound A to control fungal growth of seeds.

TABLE 26

Effect of a 10 mg/L headspace treatment of Compound A in
controlling *Aspergillus brasiliensis* growth on grains.

| | Fungal growth on PDA (mm) | | |
| --- | --- | --- | --- |
| Grains | Compound A | Control-Acetone | Control-No Acetone |
| Barley | 0 | 12.8 | 21.7 |
| Corn Dry | 0 | 10.1 | 22.8 |
| Millet | 0 | 7.2 | 19.1 |
| Rice | 0 | 7.5 | 21.6 |
| Rye | 0 | 8.4 | 21 |
| Wheat | 0 | 8.1 | 22.4 |

Grains consisting of corn, wheat, rice, rye, millet and barley are surface sterilized with 0.825% NaOCl for 1 minute and rinsed thrice with sterile distilled water. The grains are inoculated by soaking them in a $1 \times 10^6$ spores/mL suspension of *Aspergillus brasiliensis* for 1 minute. The excess inoculum is blotted out with a sterile paper towel before plating five seeds in a Petri plate containing 25 mL of PDA. For determination of efficacy, Compound A is diluted in acetone and added to 42.5 mm Whatman #1 filter disks (Cat. No. 1001-042) attached to the inner side of the lid in a dose dependent manner to achieve a final headspace concentration of 0.4, 2, or 10 mg/L. The acetone is permitted to evaporate for five minutes before closing plate and sealing it with parafilm. The plates are incubated at 23° C. for three days. After storage, the grains are evaluated for mycelial colony diameter (mm), with results summarized in Table 26. Results demonstrate 100% control of *Aspergillus brasiliensis* in this in vivo analysis.

Example 28

To evaluate a combination treatment of Compound A with 1-methylcyclopropene (1-MCP), an in vivo experiment is performed on white roses.

TABLE 27

*Botrytis cinerea* incidence and severity based on infection on petals
and sepals of white roses after a 24 hours treatment with 1-MCP
followed by a three day volatile treatment of Compound A
at 21° C. and an additional five days at 21° C.

| Treatments | Incidence (%) | Severity* (0-4) |
| --- | --- | --- |
| Control | 66.7 | 2.0 |
| 1-MCP | 33.3 | 0.4 |
| 0.008 mg/L | 20.0 | 0.2 |
| 0.04 mg/L | 20.0 | 0.03 |
| 0.2 mg/L | 0.0 | 0.0 |
| 0.008 mg/L + 1-MCP | 6.7 | 0.9 |
| 0.04 mg/L + 1-MCP | 0.0 | 0.0 |
| 0.2 mg/L + 1-MCP | 0.0 | 0.0 |

*Severity Rating
0 = No disease
1 = Browning and small lesions on the sepals or petals
2 = Browning, petals covered with fungal spores
3 = Browning, petals covered with fungal spores, some petal drop
4 = Browning, petals covered with fungal spores, some flowers aborted Five white roses are placed in an 800 mL jar containing 200 mL of a common commercial flower preservative. Three jars are then placed in a 117 L Rubbermaid storage box (Cat #2244). Two small fans are placed in opposite ends of the container to assist with the distribution of the two volatiles. A 500 parts per billion (ppb) volume per volume (v/v) 1-MCP treatment is applied (AgroFresh, Springhouse, Pa.) for 24 hours at 21° C. After the 1-MCP treatment is completed, the containers are vented, and Compound A powder is applied in a dose dependent manner to achieve a final headspace concentration of 0.2, 0.04, or 0.008 mg/L with a sublimation device (copper tube heated to 200° C. with fan flow at 0.5 L/min), with the end of the tube penetrating through a ½ inch side port in the container that is sealed immediately after the application. The flowers are incubated for three days at 21° C. After treatment, the flowers are evaluated for an additional seven days at 21° C. for disease incidence and severity of the flower petals. Results listed in Table 27 show good antimicrobial activity against *Botrytis cinerea* infection of white roses, and that enhancing the rate of volatilization through sublimation resulted in greater disease control. Also treatment with 1-MCP shows reduced petal drop as reflected by severity scores.

Example 29

To evaluate a combination treatment of Compound A with 1-methylcyclopropene (1-MCP), an in vivo experiment is performed on broccoli.

TABLE 28

Effects of Compound A and 1-MCP in controlling *Alternaria* rot and yellowing of broccoli, respectively, five or three days treatment at 10 or 21° C. with additional two days at 21° C.

| Treatments (mg/L) | 21° C. | | 11 C. | |
|---|---|---|---|---|
| | Severity | Color Score* | Severity | Color Score* |
| Control | 1.5 | 2.39 | 0.18 | 1.55 |
| 1-MCP | 0.61 | 1.79 | 0.18 | 1.50 |
| 0.4 mg/L | 0.29 | 1.32 | 0.00 | 1.75 |
| 2 mg/L | 0.07 | 1.89 | 0.00 | 2.11 |
| 0.4 mg/L + 1-MCP | 0.21 | 0.93 | 0.00 | 1.39 |
| 2 mg/L + 1-MCP | 0.07 | 1.93 | 0.00 | 2.23 |

Color Score Rating
0 = green, regular looking broccoli
1 = Few light green spots
2 = Light green and yellow spots
3 = Light green, yellow and some brown
4 = Mostly yellow and brown Broccoli flowers are inoculated with $1\times10^6$ spores/mL of *Alternaria alternata* and then placed in a 117 L Rubbermaid storage box (Cat #2244) with two small fans placed in opposite ends of the container. A 500 ppb v/v 1-MCP treatment is applied (AgroFresh, Springhouse, Pa.) for 24 hours at 1° C. After completion of the 1-MCP treatment, broccoli florets are removed and placed in a 10.8-cup SnapWare airtight container (Model #109842). Compound A powder is applied in a dose dependent manner to achieve a final headspace concentration of 2 or 0.4 mg/L with a sublimation device (copper tube heated to 200° C. with fan flow at 0.5 L/min), with the end of the tube penetrating through a ½ inch side port in the container that is sealed immediately after the application. The florets are incubated for five days at 10° C. or three days at 21° C., then evaluated for an additional five days at 21° C. for disease incidence and severity. Results listed in Table 28 show good antimicrobial activity against *Alternaria alternata* infection.

Example 30

To evaluate a combination treatment of Compound A with 1-methylcyclopropene (1-MCP), an in vivo experiment is performed on tomato. Each tomato fruit is wounded three times and inoculated with $1\times10^6$ spores/mL of *Alternaria alternata* and then placed in a 117 L Rubbermaid storage box (Cat #2244) with two small fans placed in opposite ends of the container. A 1000 ppb v/v 1-MCP treatment is applied (AgroFresh, Springhouse, Pa.) for 24 hours at 21° C. After completion of the 1-MCP treatment, the tomatoes are removed and placed in a 10.8-cup SnapWare airtight container (Model #109842). Compound A powder is applied in a dose dependent manner to achieve a final headspace concentration of 2 or 0.4 mg/L with a sublimation device (copper tube heated to 200° C. with fan flow at 0.5 L/min), with the end of the tube penetrating through a ½ inch side port in the container that is sealed immediately after the application. The tomatoes are incubated for three days at 21° C., then evaluated for an additional three days at 21° C. for disease incidence and severity. Results listed in Table 29 show good activity against *Alternaria alternata* infection of tomato.

TABLE 29

Effects of Compound A and 1-MCP in controlling *Alternaria* rot on tomatoes, three days treatment at 21° C. with additional three days at 21° C.

| Compound A | Diameter of the rot (mm) |
|---|---|
| Control | 14.8 |
| 1-MCP | 13.6 |
| 0.4 mg/L | 3.8 |
| 2 mg/L | 0.0 |
| 0.4 mg/L + 1-MCP | 3.8 |
| 2 mg/L + 1-MCP | 0.0 |

Example 31

To assess the in vivo activity of volatile antimicrobial Compounds A and B (FIG. 1) in fruit, a volatile bioassay is developed using apple, pear, orange, strawberry, grape and blueberry.

TABLE 30

Effects of subliming Compounds A and B as reflected by incidence and severity of *B. cinerea* on strawberry, grape and blueberry, and severity on oranges, apples and pears as depicted by water soaked lesions, browning and sporulation after a three day treatment plus an additional three days at 21° C.

| Treatments | Incidence (%) | | | Severity (0-4) | | |
|---|---|---|---|---|---|---|
| (1 mg/L) | Strawberry | Blueberry | Grape | Strawberry | Blueberry | Grape |
| Compound A | 0.0 | 0.0 | 0.0 | 0.0 | 0.0 | 0.0 |
| Compound B | 0.0 | 0.0 | 0.0 | 0.0 | 0.0 | 0.0 |
| Control | 100.0 | 100.0 | 100.0 | 3.9 | 2.5 | 1.9 |

TABLE 30-continued

Effects of subliming Compounds A and B as reflected by incidence and severity of B. cinerea on strawberry, grape and blueberry, and severity on oranges, apples and pears as depicted by water soaked lesions, browning and sporulation after a three day treatment plus an additional three days at 21° C.

|  | Water soaked lesion | Browning (mm) | | Sporulation (mm) | | |
| --- | --- | --- | --- | --- | --- | --- |
|  | Orange | Apple | Pear | Apple | Orange | Pear |
| Compound A | 0.0 | 0.8 | 4.7 | 0.0 | 0.0 | 0.0 |
| Compound B | 0.0 | 2.3 | 1.1 | 0.2 | 0.0 | 0.0 |
| Control | 73.2 | 21.7 | 29.7 | 46.0 | 5.2 | 18.5 |

Two apples, 2 oranges, 2 pears, 8 strawberries, 16 grapes or 30 blueberries (per replicate, in duplicate) are placed in a clamshell with the stem end facing up for all fruits except for strawberry (stem end facing downwards). A fresh wound is inoculated with 20 μL 1×10$^6$ per mL *Penicillium expansum* spore suspension (apple and pear), 20 μL 1×10$^6$ per mL *Penicillium digitatum* spore suspension (orange), and 20 μL (strawberry and grape) or 10 μL (blueberry) of 1×10$^6$ per mL *Botrytis cinerea* spore suspension. The clamshells are placed inside a 117 L Rubbermaid storage box (Cat #2244) with lids closed. Compound A and B powders are introduced to the containers by a sublimation device (copper tube heated to 200° C. with fan flow at 0.5 L/min) to achieve a final headspace concentration of 1 mg/L. The containers are then held for three days at 21° C. After treatment, fruits are held for an additional three days at 21° C., then evaluated for disease incidence (mm diameter of browning or water-soaked lesions) and pathogen sporulation (mm diameter) for apple, pear and orange, as well as *Botrytis cinerea* disease incidence (%) and severity (0 to 4) for strawberry, grape and blueberry, with results summarized in Table 30. Results demonstrate 100% in vivo antimicrobial control of *B. cinerea* and *P. digitatum* by both Compounds A and B on different hosts when applied as a volatile fungicide.

Example 32

In order to assess the activity of Compound A as a contact fungicide, an in vitro assay is developed. A 6 cm-diameter Petri plate is used. Compound A is amended into full-strength Potato Dextrose Agar (PDA) to achieve a final solution concentration of 10, 2, 0.4, or 0.08 mg/L, and 15-mL volume of solution is added to each plate. After cooling, 1 μL of 1×10$^5$ per mL *Penicillium expansum* or *Penicillium digitatum* spore suspension is spot-pipetted into the center of the agar.

Plates are sealed with a parafilm and placed in an incubator held at 23° C. After three days of storage, the cultures are evaluated for percent growth relative to control based on measurement of fungal colony diameter. Experimental results are summarized in Table 31. The results indicate that Compound A has activity as a contact fungicide in this in vitro assay against plant fungal pathogens.

TABLE 31

The in vitro MIC for Compound A as a contact fungicide for mycelial growth inhibition of *Penicillium expansum* and *Penicillium digitatum*.

| Pathogen | Incidence (%) | |
| --- | --- | --- |
| Rate (mg/L) | *P. expansum* | *P. digitatum* |
| 10 | 0.0 | 0.0 |
| 2 | 0.0 | 0.0 |
| 0.4 | 33.0 | 12.5 |
| 0.08 | 93.1 | 42.0 |

Example 33

In order to assess the activity of Compound A (FIG. 1) as a contact drench fungicide, an in vivo assay is developed. Two apples or 2 oranges (per replicate, in duplicate) are placed in a clamshell, and three fresh wounds near the equatorial region of each fruit are made. Compound A is dissolved in water to achieve a final treatment solution concentration of 250, 50, or 10 mg/L. The fruit is dipped in Compound A solution for 1 minute and allowed to dry for 1 hour. Fruit wounds are then inoculated with 30 μL of 1×10$^6$ per mL *Penicillium expansum* spore suspension (apple) or *Penicillium digitatum* spore suspension (orange). Clamshells are then placed in a 10.8-cup SnapWare airtight container (Model #109842) and incubated for 3 days at 21° C. After treatment, the fruit is held for an additional 3 days at 21° C. and then evaluated for disease incidence (mm diameter of browning or water-soaked lesions) and pathogen sporulation (mm diameter), with results summarized in Table 32. Results demonstrate good in vivo antimicrobial control of 2 fungal pathogens on 2 different hosts when applied as a contact fungicide.

TABLE 32

In vivo MIC for Compound A as a contact fungicide for control of *Penicillium digitatum* and *Penicillium expansum* on oranges and apples respectively.

| | Oranges | | Apples | |
| --- | --- | --- | --- | --- |
| Compound A (mg/L) | Water soaked (mm) | Sporulation (mm) | Browning (mm) | Sporulation (mm) |
| Control | 42.7 | 31.0 | 9.7 | 3.5 |
| 10 | 27.5 | 16.6 | 8.5 | 2.1 |
| 50 | 18.8 | 12.0 | 3.7 | 1.6 |
| 250 | 1.7 | 0.4 | 0.8 | 0.5 |

Example 34

In order to assess the activity of Compound A as a volatile fungicide, an in vitro assay is developed to evaluate spore germination. Two mL of water agar is poured in 3.5 cm Petri plates. Compound A is dissolved in acetone to achieve a final treatment solution concentration of 0.14, 0.07, or 0.035 mg/L. Plates are inoculated with 1 μL 1×10$^6$ per mL *Botrytis cinerea* and *Penicillium expansum* spore suspension. Plates are then incubated for either one day at 0° C., five day at 0° C., or five day at 0° C. plus an additional one or two days at 21° C. At each time point, plates are removed and 100 spores are counted for percent germination, where germination is defined as a germ tube that has extended a distance greater than the length of the spore. Results are summarized in Table 33. At all three treatment concentrations and temperature regimes, Compound A completely inhibits the germination of the fungal pathogens spores tested.

TABLE 33

Percent germination of *Botrytis cinerea* and *Penicillium expansum* spores in response to a volatile treatment with Compound A under 4 different temperature regimes

| Pathogens | Compound A Rate (mg/L) | Germination Inhibition (%) | | | |
|---|---|---|---|---|---|
| | | 1 day, 0° C. | 5 day, 0° C. | 5 day, 0° C. 1 day, 21° C. | 5 day, 0° C. 2 day, 21° C. |
| B. cinerea | 0.14 | 0.0 | 0.0 | 0.0 | 0.0 |
| | 0.07 | 0.0 | 0.0 | 0.0 | 0.0 |
| | 0.035 | 0.0 | 0.0 | 0.0 | 0.0 |
| | Control | 44.8 | 98.7 | 92.2 | 98.4 |
| | Acetone | 48.9 | 98.9 | 93.9 | 95.8 |
| P. expansum | 0.14 | 0.0 | 0.0 | 0.0 | 0.0 |
| | 0.07 | 0.0 | 0.0 | 0.0 | 0.0 |
| | 0.035 | 0.0 | 0.0 | 0.0 | 0.0 |
| | Control | 0.0 | 1.1 | 12.6 | 30.8 |
| | Acetone | 0.0 | 0.0 | 6.4 | 21.8 |

Example 35

In order to assess the activity of Compound A as a volatile fungicide, an in vitro assay is developed to evaluate spore germination. 3.5-cm Petri plates are filled with 2 mL of water agar. After cooling, 1 μL of 1×10$^5$ per mL *Botrytis cinerea* spore suspension is spot-pipetted into the center of the plate. Plates are inoculated immediately prior to volatile fungicide treatment. A Whatman #1 filter disk (Cat. No. 1001-0155) is placed, in duplicate, on the underside of a plate lid. For determination of the minimum inhibitory concentration (MIC), compounds are diluted in acetone, and the appropriate amount of compound is added to the disks in a dose dependent manner to achieve a final headspace concentration of 142.9 to 0.07 mg/L. The acetone is permitted to evaporate for five minutes, and then the lids are placed on the plates and sealed with parafilm. After 24 hours of storage at 23° C., 100 spores are counted for percent germination, where germination is defined as a germ tube that has extended a distance greater than the length of the spore. After counting, treatment is removed, and the plates are resealed. After an additional 24 hours, 100 spores are again counted. Plugs are then transferred to a clean plate containing full-strength PDA and allowed to incubate at 23° C. for an additional three days. After incubation, mycelial growth (mm diameter) is determined and summarized in Table 34. After 24 hours, 100% of the control spores have germinated while all rates of Compound A resulted in 100% inhibition of germination in this volatile in vitro assay. These results show that Compound A delivers a fungicidal effect, as opposed to a fungistatic effect, such that treated spores fail to germinate and grow as mycelia even after the compound has been removed.

TABLE 34

Spore germination and subsequent mycelial growth after transfer to fresh media of *Botrytis cinerea* in response to a volatile treatment of Compound A.

| Compound A Rate (mg/L) | Spore germination (%) | | Mycelial growth after transfer (%) |
|---|---|---|---|
| | 24 h$^a$ | 24 h + 24 h$^b$ | 3 d$^c$ |
| Control | 100.0 | 100.0 | 100.0 |
| Acetone | 98.4 | 92.7 | 100.0 |
| 142.9 | 0.0 | 0.0 | 0.0 |
| 71.4 | 0.0 | 0.0 | 0.0 |
| 35.7 | 0.0 | 0.0 | 0.0 |
| 17.9 | 0.0 | 0.0 | 0.0 |
| 8.9 | 0.0 | 0.0 | 0.0 |
| 4.5 | 0.0 | 0.0 | 10.1 |
| 2.2 | 0.0 | 0.0 | 16.9 |
| 1.1 | 0.0 | 0.0 | 32.6 |
| 0.56 | 0.0 | 0.0 | 43.3 |
| 0.28 | 0.0 | 0.0 | 51.3 |
| 0.14 | 0.0 | 0.0 | 53.8 |
| 0.07 | 0.0 | 10.0 | 60.3 |

$^a$Spore germination determined after 24 hours treatment
$^b$Spore germination determined after additional 24 hours after treatment removal
$^c$Percent mycelial growth 3 days after transfer of inoculum to clean PDA plates

We claim:

1. A method of using a volatile antimicrobial compound against pathogens affecting meats, plants, or plant parts, comprising providing in gaseous form a volatile antimicrobial compound of formula (IV):

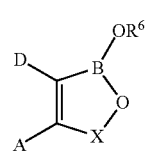

(IV)

contacting a meat, plant, or plant part with an effective amount of the volatile antimicrobial compound in gaseous form; and contacting the meat, plant, or plant part with an effective amount of a cyclopropene compound in gaseous form;

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

X is a group —CR$^7$R$^8$ wherein R$^7$ and R$^8$ are each independently hydrogen, $C_1$-$C_6$-alkyl, nitrile, nitro, aryl, arylalkyl or R$^7$ and R$^8$ together with the carbon atom to which they are attached form an alicyclic ring; and R$^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

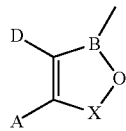
(V)

wherein A, D and X are as defined herein before except for boronophthalide;
and agriculturally acceptable salts thereof.

2. The method of claim 1, wherein the pathogen is at least one member selected from the group consisting of *Acremonium* spp., *Albugo* spp., *Alternaria* spp., *Ascochyta* spp., *Aspergillus* spp., *Bacillus* spp., *Botryodiplodia* spp., *Botryospheria* spp., *Botrytis* spp., *Byssochlamys* spp., *Campylobacter* spp., *Candida* spp., *Cephalosporium* spp., *Ceratocystis* spp., *Cercospora* spp., *Chalara* spp., *Cladosporium* spp., *Clavibacter* spp., *Clostridium* spp., *Colletotrichum* spp., *Cryptosporidium* spp., *Cryptosporiopsis* spp., *Cylindrocarpon* spp., *Debaryomyces* spp., *Diaporthe* spp., *Didymella* spp., *Diplodia* spp., *Dothiorella* spp., *Elsinoe* spp., *Erwinia* spp., *Escherichia* spp., *Fusarium* spp., *Geotrichum* spp., *Giardia* spp., *Gloeosporium* spp., *Glomerella* spp., *Helminthosporium* spp., *Khuskia* spp., *Lactobacillus* spp., *Lasiodiplodia* spp., *Leuconostoc* spp., *Listeria* spp., *Macrophoma* spp., *Macrophomina* spp., *Microdochium* spp., *Monilinia* spp., *Monilochaethes* spp., *Mucor* spp., *Mycocentrospora* spp., *Mycosphaerella* spp., *Nectria* spp., *Neofabraea* spp., *Nigrospora* spp., *Pantoea* spp., *Pectobacterium* spp., *Penicillium* spp., *Peronophythora* spp., *Peronospora* spp., *Pestalotiopsis* spp., *Pezicula* spp., *Phacidiopycnis* spp., *Phoma* spp., *Phomopsis* spp., *Phyllosticta* spp., *Phytophthora* spp., *Polyscytalum* spp., *Pseudocercospora* spp., *Pseudomonas* spp., *Pyricularia* spp., *Pythium* spp., *Ralstonia* spp., *Rhizoctonia* spp., *Rhizopus* spp., *Salmonella* spp., *Sclerotium* spp., *Sclerotinia* spp., *Septoria* spp., *Shigella* spp., *Sphaceloma* spp., *Sphaeropsis* spp., *Staphylococcus* spp., *Stemphyllium* spp., *Stilbella* spp., *Thielaviopsis* spp., *Thyronectria* spp., *Trachysphaera* spp., *Uromyces* spp., *Ustilago* spp., *Venturia* spp., *Verticillium* spp., *Vibrio* spp., *Xanthomonas* spp., and *Yersinia* spp.

3. The method of claim 1, wherein the method comprises a treatment selected from the group consisting of treatment during field packing, treatment in clamshells, treatment during palletization or after palletization, treatment in open pallets or in wrapped pallets, treatment in tents, treatments inside boxes with or without liners, in sea container, truck or other container types used during transportation, and treatment during storage.

4. The method of claim 1, wherein the plants or plant parts are selected from the group consisting of asparagus, sugar beet, barley, broccoli, cabbage, carrot, cassava, cauliflower, celery, cucumber, eggplant, garlic, grapevine, lettuce, spinach, leek, mushroom, onion, peas, pepper, bell pepper, potato, pumpkin, rye, sweet potato, squash, tobacco, tomato, snap bean, sorghum, sugarcane, corn, wheat, cotton, rice, soybean, canola, fruit, vegetables, nursery, turf, flowers, carnation, geranium, lily, orchid, rose, sunflower, ornamental flowers and ornamental crops.

5. The method of claim 4, wherein the fruit is selected from the group consisting of apple, avocado, banana, strawberry, blueberry, raspberry, blackberry, cherry, oranges, lemon, lime, grapefruit, fig, grapes, guava, kiwifruit, mango, nectarine, cantaloupe, muskmelon, watermelon, papaya, peach, pear, persimmon, pineapple, and pomegranate.

6. The method of claim 4, wherein the meat is selected from the group consisting of beef, bison, chicken, deer, goat, turkey, pork, sheep, fish, shellfish, mollusks and dry-cured meat products.

7. The method of claim 1, wherein the contacting comprises applying the volatile antimicrobial compound by a gas treatment selected from the group consisting of release from a sachet, release from a synthetic or natural film, release from liner or other packaging materials, release from powder, release from a gas-releasing generator, release using a compressed or non-compressed gas cylinder, release from a droplet or droplets placed inside a box, release from a mist or fog applied into a container and combinations thereof.

8. The method of claim 1, wherein the volatile antimicrobial compound has a structure of

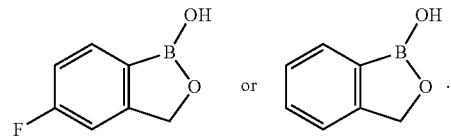 [SMILES: OB1OCc2cc(F)ccc21 ; "or" ; OB1OCc2ccccc21 ; "."]

9. A method of using a volatile antimicrobial compound against pathogens affecting meats, plants, or plant parts, comprising placing a meat, plant or plant part in a container;
introducing into the container and in contact with the meat, plant or plant part an effective amount of a gaseous form of a volatile antimicrobial compound of formula (IV):

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;
X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and
$R^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

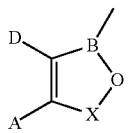

(V)

wherein A, D and X are as defined herein before except for boronophthalide; and agriculturally acceptable salts thereof; and introducing into the container and in contact with the meat, plant or plant part an effective amount of 1-methylcyclopropene (1-MCP).

10. The method of claim 9, wherein the method comprises a treatment selected from the group consisting of treatment during field packing, treatment in clamshells, treatment during palletization or after palletization, treatment in open pallets or in wrapped pallets, treatment in tents, treatments inside boxes with or without liners, in sea container, truck or other container types used during transportation, and treatment during storage.

11. The method of claim 9, wherein the plants or plant parts are selected from the group consisting of asparagus, sugar beet, barley, broccoli, cabbage, carrot, cassava, cauliflower, celery, cucumber, eggplant, garlic, grapevine, lettuce, spinach, leek, mushroom, onion, peas, pepper, bell pepper, potato, pumpkin, rye, sweet potato, squash, tobacco, tomato, snap bean, sorghum, sugarcane, corn, wheat, cotton, rice, soybean, canola, fruit, vegetables, nursery, turf, flowers, carnation, geranium, lily, orchid, rose, sunflower, ornamental flowers and ornamental crops.

12. The method of claim 11, wherein the fruit is selected from the group consisting of apple, avocado, banana, strawberry, blueberry, raspberry, blackberry, cherry, oranges, lemon, lime, grapefruit, fig, grapes, guava, kiwifruit, mango, nectarine, cantaloupe, muskmelon, watermelon, papaya, peach, pear, persimmon, pineapple, and pomegranate.

13. The method of claim 9, wherein the meat is selected from the group consisting of beef, bison, chicken, deer, goat, turkey, pork, sheep, fish, shellfish, mollusks and dry-cured meat products.

14. The method of claim 9, wherein the contacting comprises applying the volatile antimicrobial compound by a gas treatment selected from the group consisting of release from a sachet, release from a synthetic or natural film, release from liner or other packaging materials, release from powder, release from a gas-releasing generator, release using a compressed or non-compressed gas cylinder, release from a droplet or droplets placed inside a box, release from a mist or fog applied into a container and combinations thereof.

15. The method of claim 9, wherein the volatile antimicrobial compound has a structure of

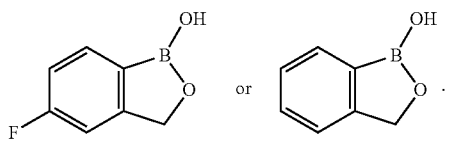

16. A method of treating plants, or plant parts, comprising contacting the plants or plant parts with an atmosphere comprising an effective amount of a volatile antimicrobial compound in gaseous form, wherein the volatile antimicrobial compound is a compound of formula (IV):

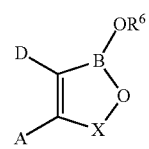

(IV)

wherein A and D together with the carbon atoms to which they are attached form a 5-, 6-, or 7-membered fused ring which may be substituted by $C_1$-$C_6$-alkyl, $C_1$-$C_6$-alkoxy, hydroxy, halogen, nitro, nitrile, amino, amino substituted by one or more $C_1$-$C_6$-alkyl groups, carboxy, acyl, aryloxy, carbonamido, carbonamido substituted by $C_1$-$C_6$-alkyl, sulfonamido or trifluoromethyl or the fused ring may link two oxaborole rings;

X is a group —$CR^7R^8$ wherein $R^7$ and $R^8$ are each independently hydrogen, $C_1$-$C_6$-alkyl, nitrile, nitro, aryl, arylalkyl or $R^7$ and $R^8$ together with the carbon atom to which they are attached form an alicyclic ring; and $R^6$ is hydrogen, $C_1$-$C_{18}$-alkyl, $C_1$-$C_{18}$-alkyl substituted by $C_1$-$C_6$-alkoxy, $C_1$-$C_6$-alkylthio, hydroxy, amino, amino substituted by $C_1$-$C_{18}$-alkyl, carboxy, aryl, aryloxy, carbonamido, carbonamido substituted by $C_1$-$C_6$-alkyl, aryl or arylalkyl, arylalkyl, aryl, heteroaryl, cycloalkyl, $C_1$-$C_{18}$-alkyleneamino, $C_1$-$C_{18}$-alkyleneamino substituted by phenyl, $C_1$-$C_6$-alkoxy or $C_1$-$C_6$-alkylthio, carbonyl alkyleneamino or a radical of formula (V):

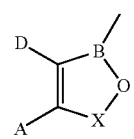

(V)

wherein A, D and X are as defined herein before except for boronophthalide; and agriculturally acceptable salts thereof; and wherein the atmosphere further comprises an effective amount of 1-methylcyclopropene (1-MCP).

17. The method of claim 16, wherein the volatile antimicrobial compound has a structure of

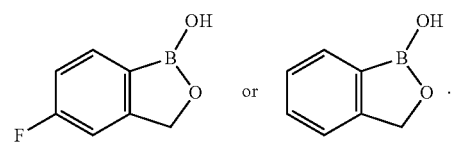 [SMILES: OB1OCc2cc(F)ccc21 ; "or" ; OB1OCc2ccccc21 ; "."]

18. The method of treatment of claim 16, wherein the method comprises a treatment selected from the group consisting of treatment during field packing, treatment in clamshells, treatment during palletization or after palletization, treatment in open pallets or in wrapped pallets, treatment in tents, treatments inside boxes with or without liners, in sea container, truck or other container types used during transportation, and treatment during storage.

* * * * *